US009668935B2

(12) United States Patent
Scovell

(10) Patent No.: US 9,668,935 B2
(45) Date of Patent: Jun. 6, 2017

(54) PACKAGE ASSEMBLY

(71) Applicant: DePuy Synthes Products, Inc., Raynham, MA (US)

(72) Inventor: Daniel Brian Scovell, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 713 days.

(21) Appl. No.: 14/077,281

(22) Filed: Nov. 12, 2013

(65) Prior Publication Data

US 2014/0131369 A1 May 15, 2014

Related U.S. Application Data

(60) Provisional application No. 61/726,132, filed on Nov. 14, 2012.

(51) Int. Cl.
| | | |
|---|---|---|
| *A61B 17/06* | (2006.01) | |
| *A61J 1/00* | (2006.01) | |
| *A61F 2/00* | (2006.01) | |
| *B65D 77/02* | (2006.01) | |

(52) U.S. Cl.
CPC .............. *A61J 1/00* (2013.01); *A61F 2/0095* (2013.01); *B65D 77/02* (2013.01)

(58) Field of Classification Search
CPC .... B65D 5/4204; B65D 5/4208; B65D 77/02; A61F 2/0095
USPC ..... 206/775–778, 782, 583, 438; 229/87.06; 220/662
See application file for complete search history.

(56) References Cited

U.S. PATENT DOCUMENTS

| | | | | |
|---|---|---|---|---|
| 2,804,258 | A | 8/1957 | Petter | |
| 3,161,288 | A * | 12/1964 | Wagner | B65D 5/4204 206/777 |
| 3,949,868 | A * | 4/1976 | Allen | B65D 5/4204 206/471 |
| 3,989,139 | A * | 11/1976 | Vargo | B65D 5/5026 206/521 |
| 5,894,932 | A * | 4/1999 | Harding | B65D 81/075 206/583 |
| 5,975,307 | A * | 11/1999 | Harding | B65D 81/075 206/583 |
| 6,237,837 | B1 | 5/2001 | Martin | |

(Continued)

FOREIGN PATENT DOCUMENTS

| | | |
|---|---|---|
| EP | 0982236 | 3/2000 |
| WO | WO 2014/078287 | 5/2014 |

OTHER PUBLICATIONS

International Search Report dated Jul. 2, 2014 for International application No. PCT/US2013/069613, 6 pages.

(Continued)

*Primary Examiner* — Luan K Bui
(74) *Attorney, Agent, or Firm* — Baker & Hostetler LLP

(57) ABSTRACT

A packaging assembly is configured to contain an object and may include an outer packaging member. The outer packing member includes an outer packaging body and an outer packaging opening that extends through the outer packaging body. The outer packaging member further includes a substantially transparent film that is attached to the outer packaging body and substantially covers the outer packaging opening.

23 Claims, 13 Drawing Sheets

(56) References Cited

U.S. PATENT DOCUMENTS

| | | | | |
|---|---|---|---|---|
| 8,051,984 B1* | 11/2011 | Johnston | ................ | B65D 27/04 |
| | | | | 206/778 |
| 8,727,123 B1* | 5/2014 | Roberts | ................ | B65D 81/075 |
| | | | | 206/521 |
| 2011/0108612 A1* | 5/2011 | Nickell | ................... | B31B 19/82 |
| | | | | 229/75 |
| 2011/0240515 A1* | 10/2011 | Ridgeway | ............ | B65D 5/5028 |
| | | | | 206/583 |
| 2011/0309073 A1 | 12/2011 | Dacey et al. | | |
| 2014/0183097 A1* | 7/2014 | LeRoy | ................ | B65D 75/305 |
| | | | | 206/583 |

OTHER PUBLICATIONS

Written Opinion, Jul. 7, 2014 for International application No. PCT/US2013/069613, 6 pages.
U.S. Appl. No. 61/726,132, filed Nov. 14, 2012, Scovell.

* cited by examiner

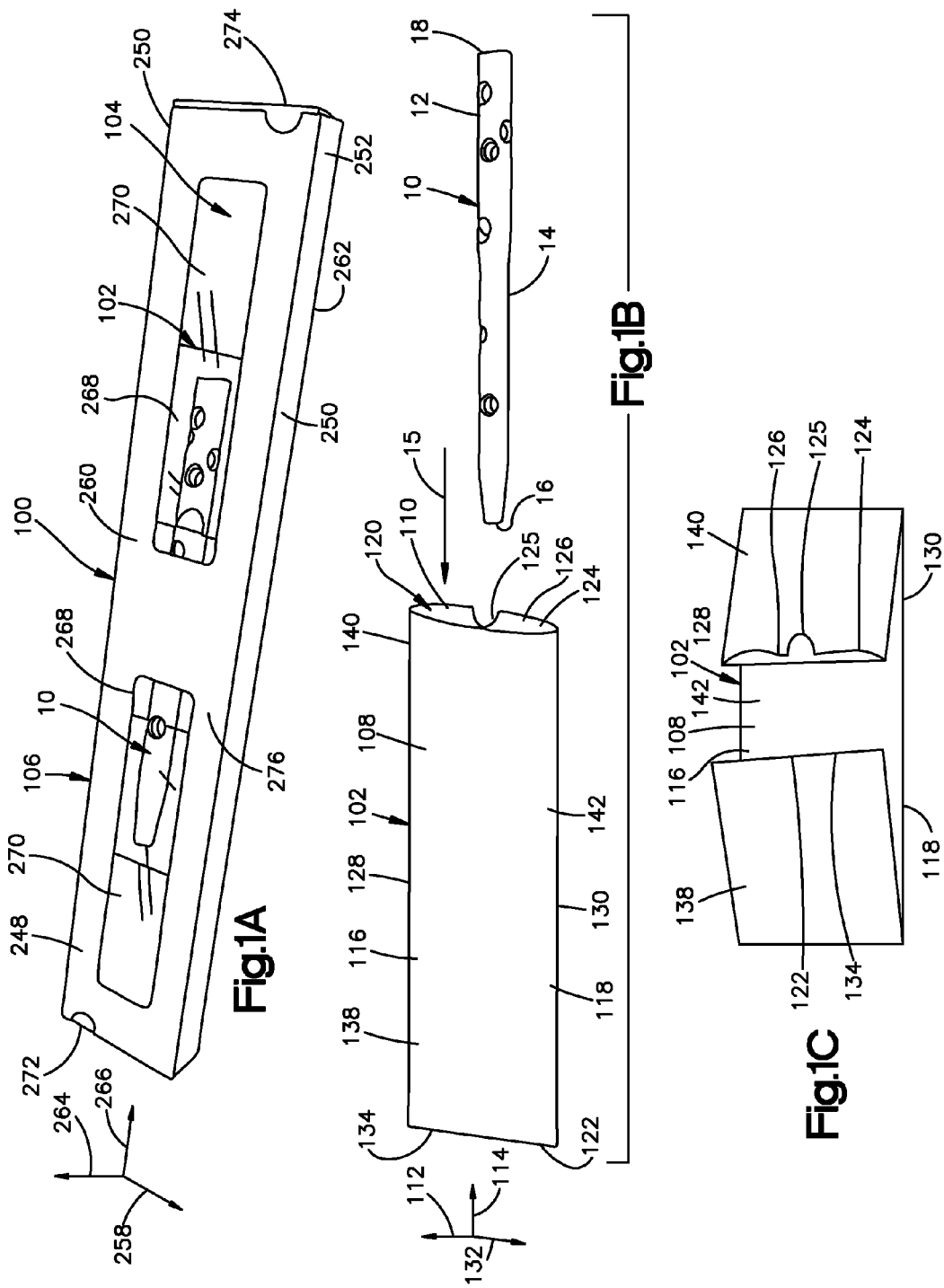

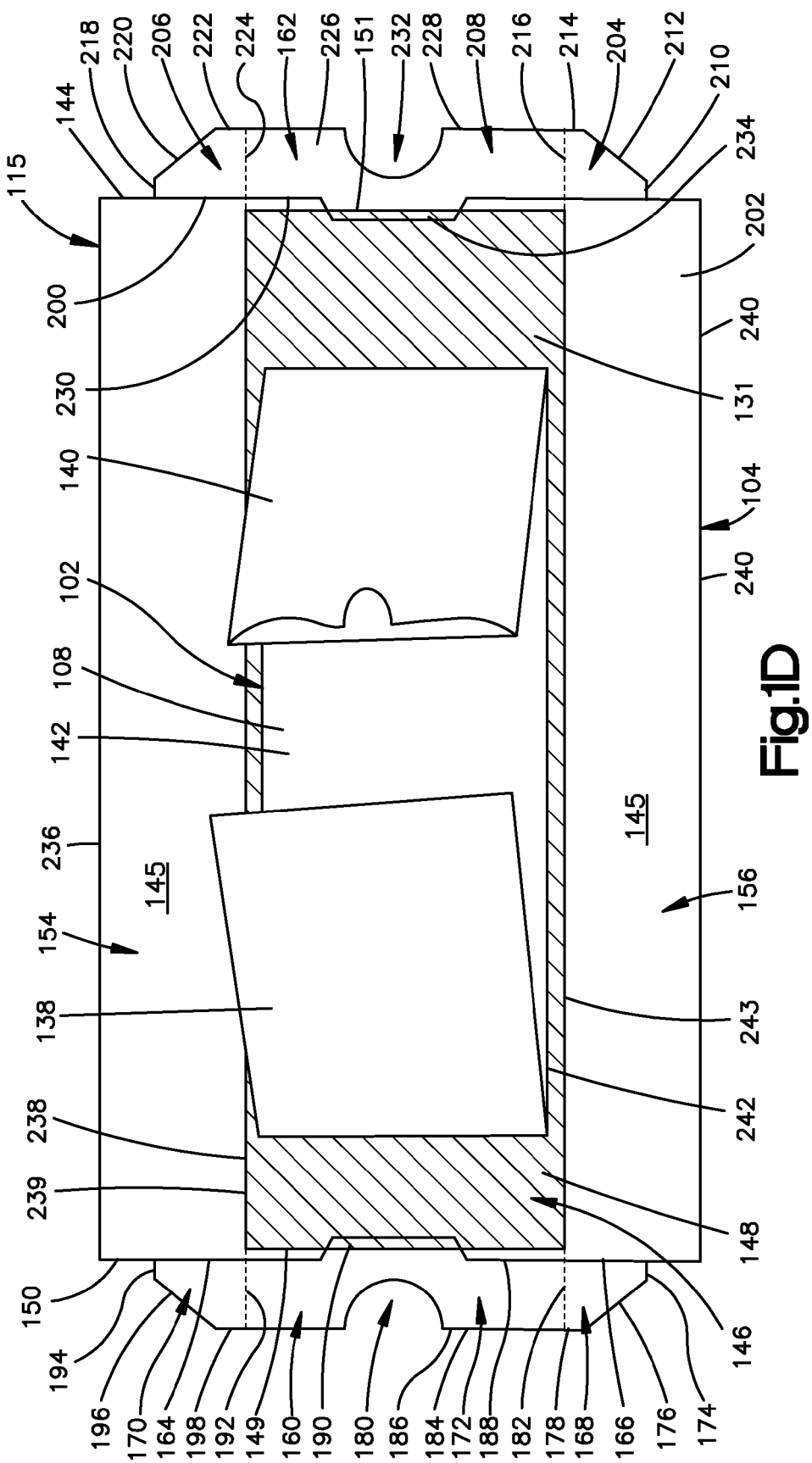

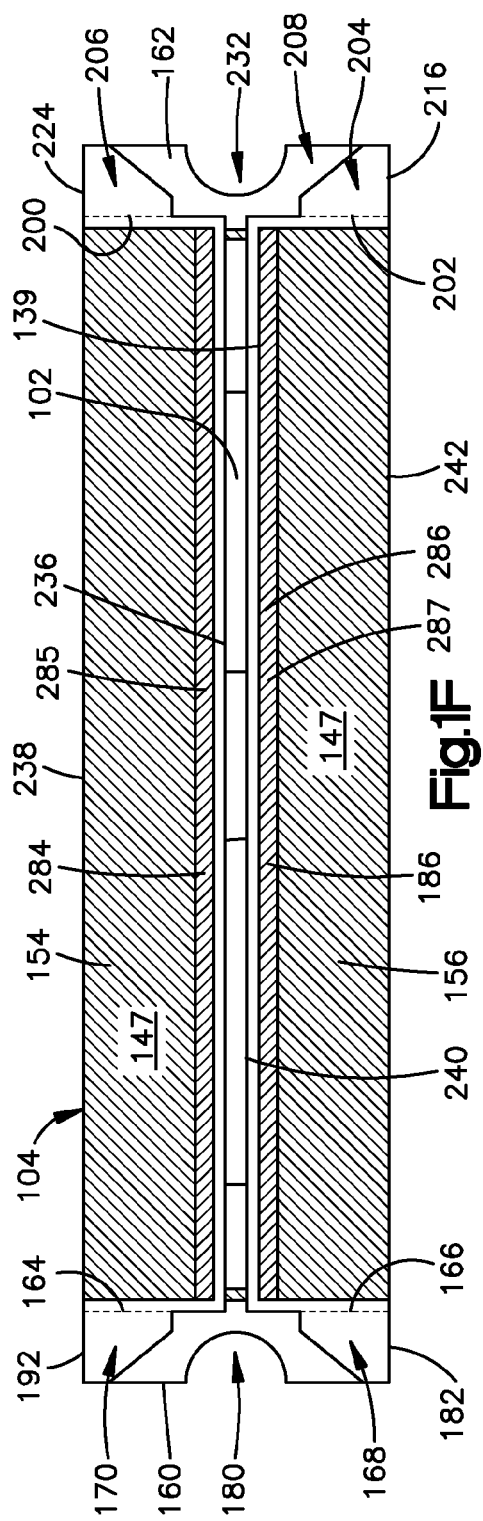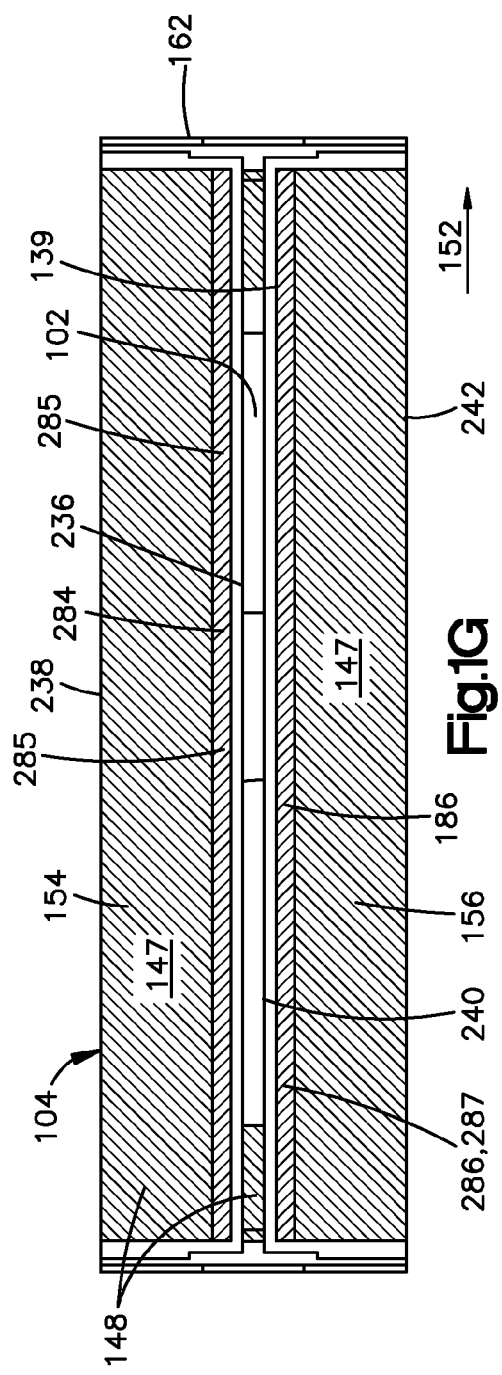

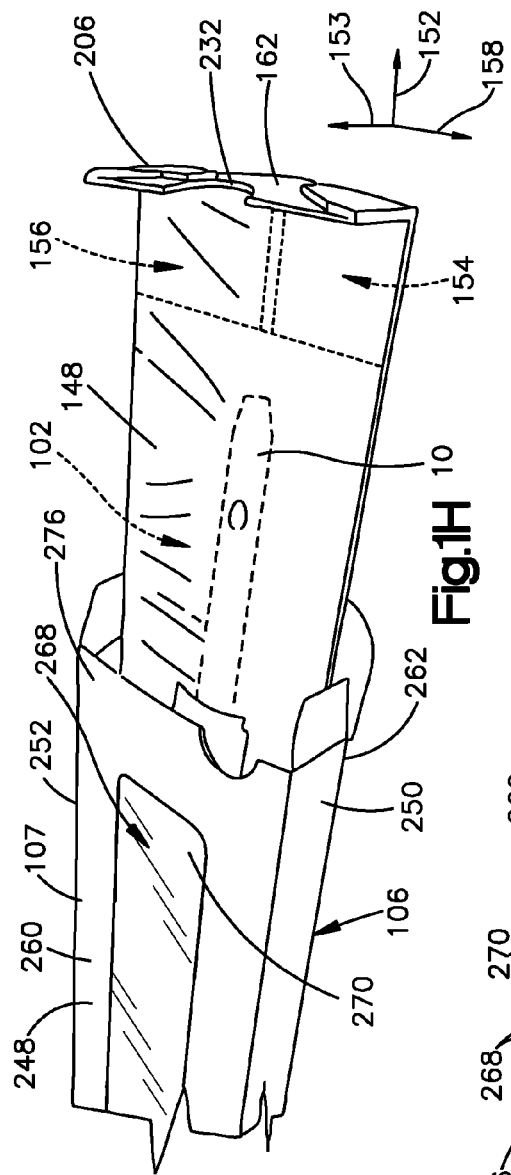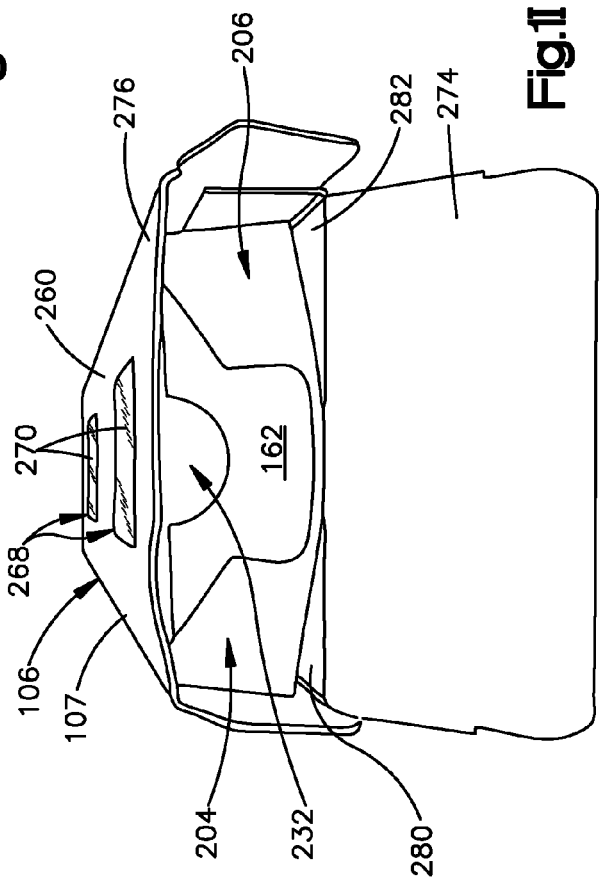

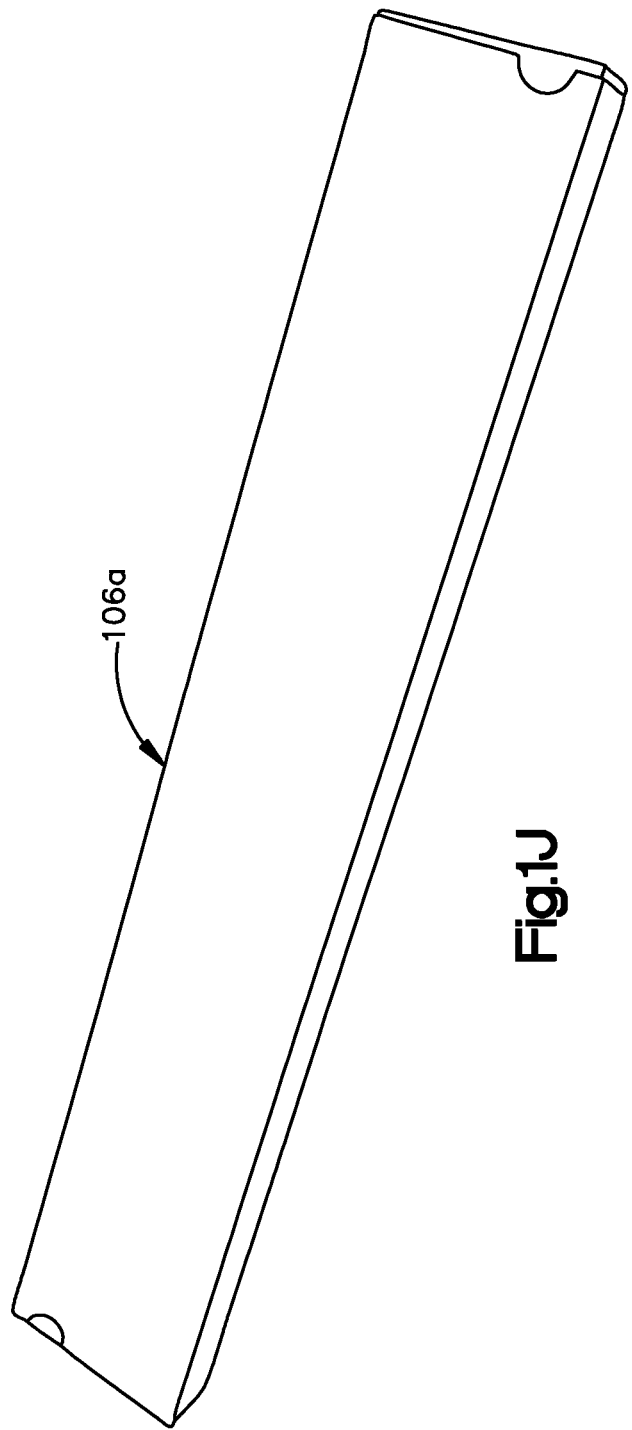

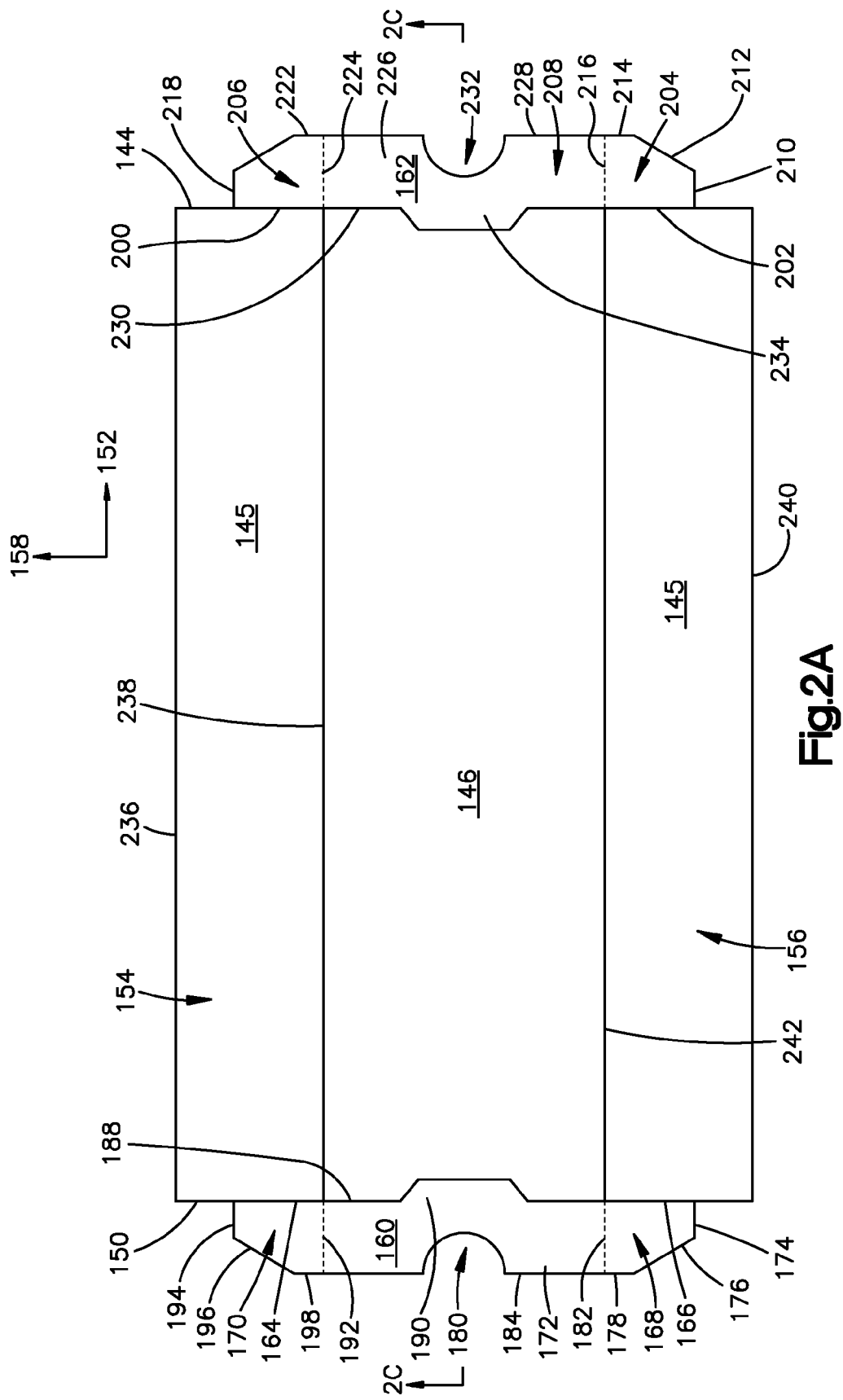

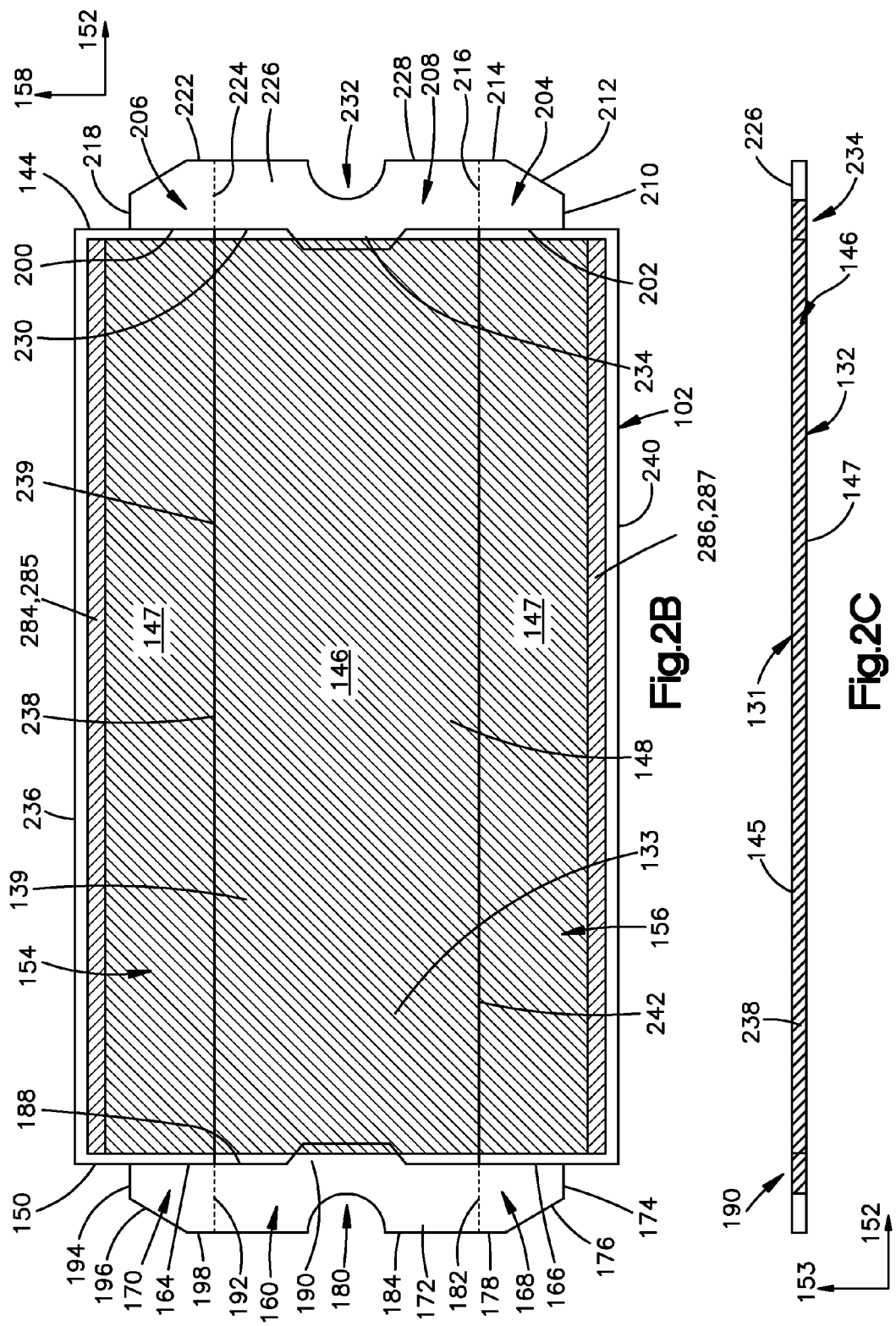

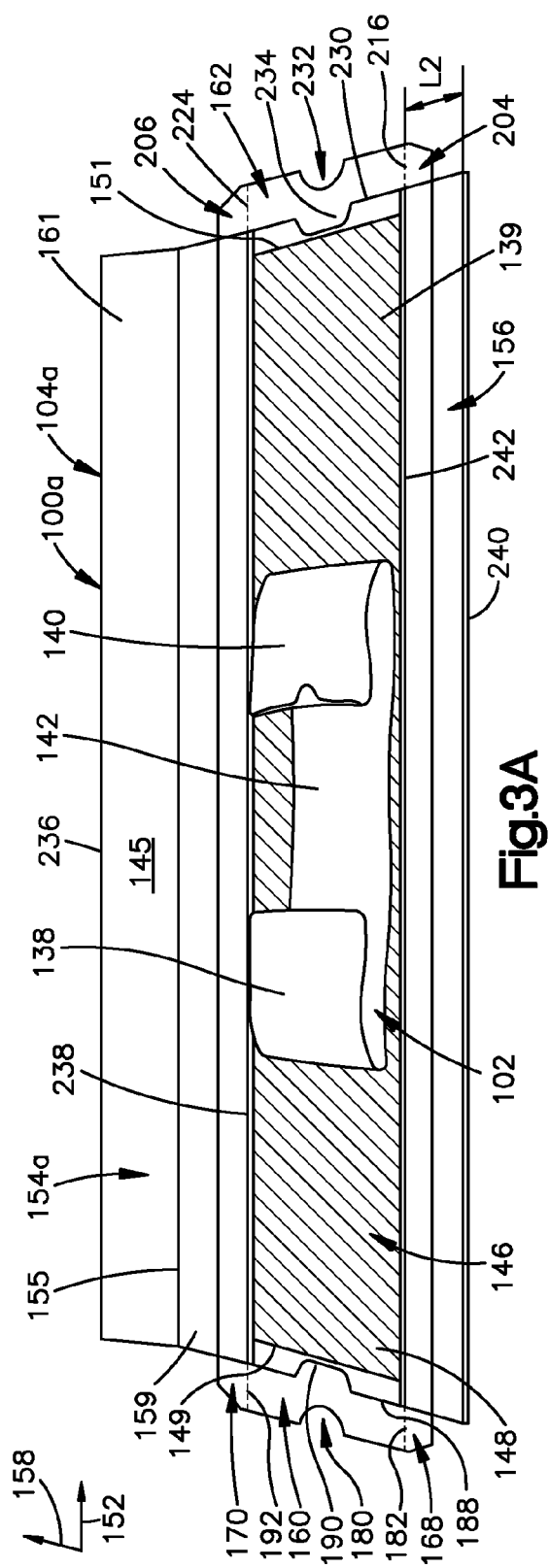
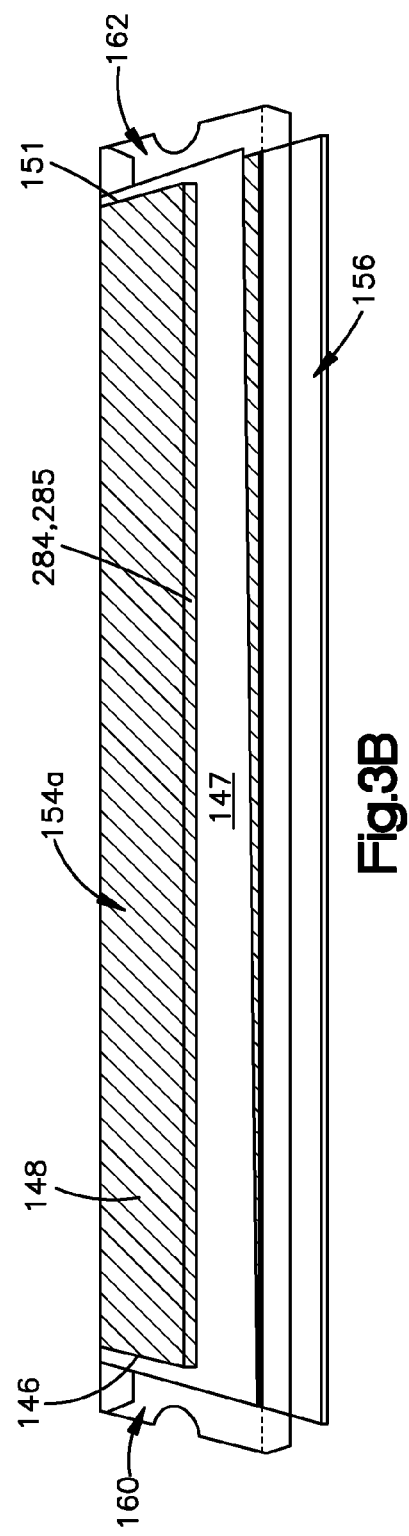
Fig.3A
Fig.3B

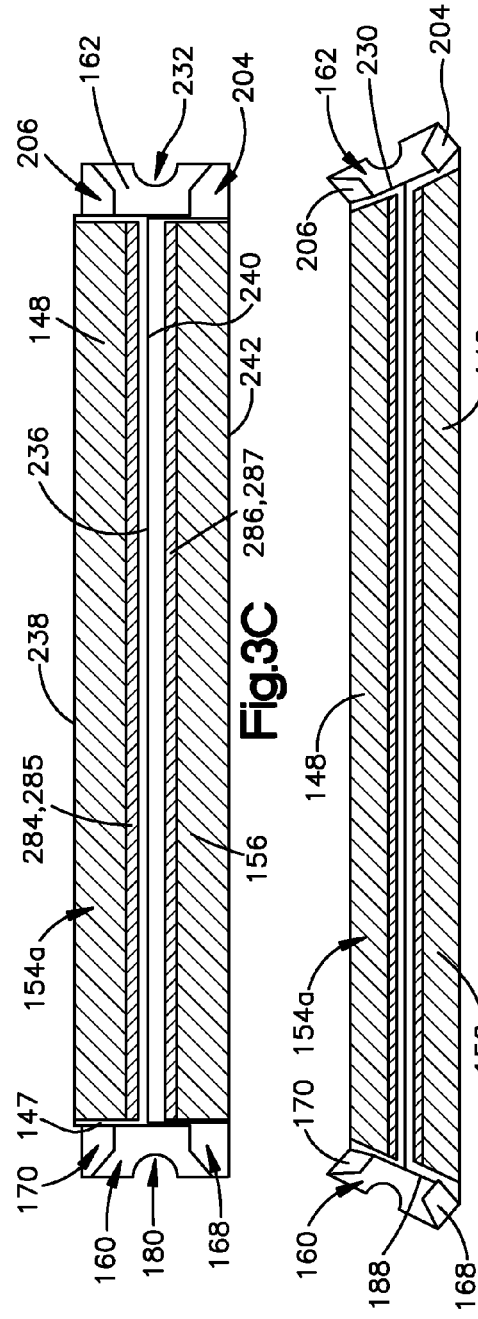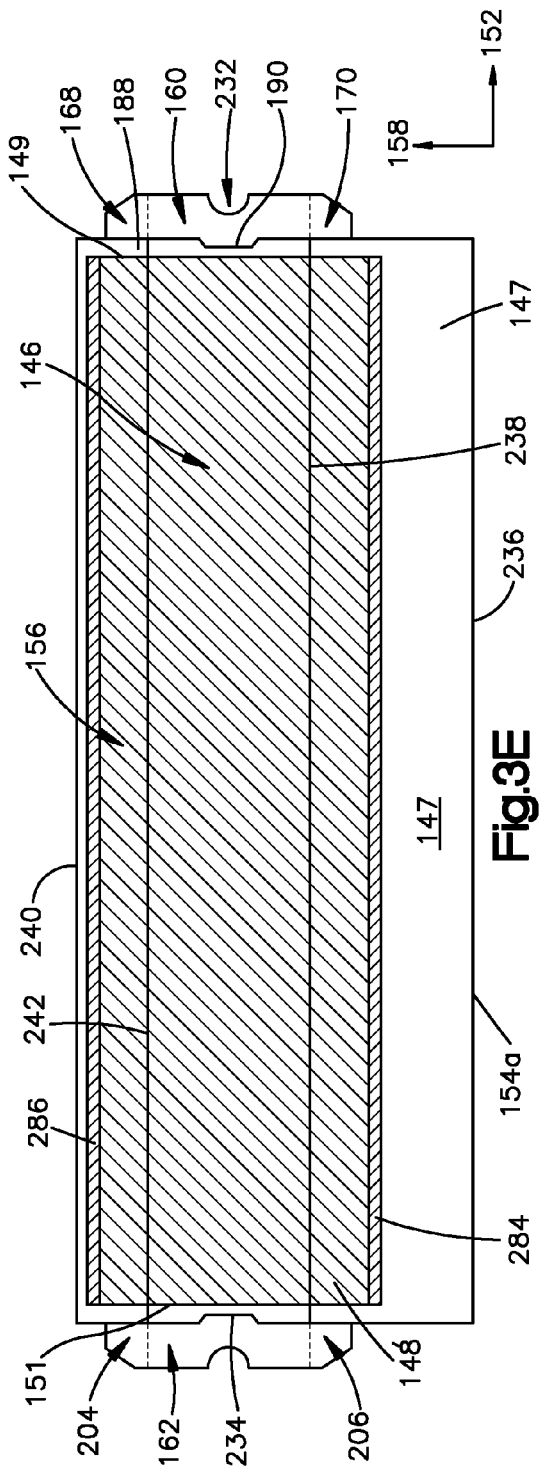

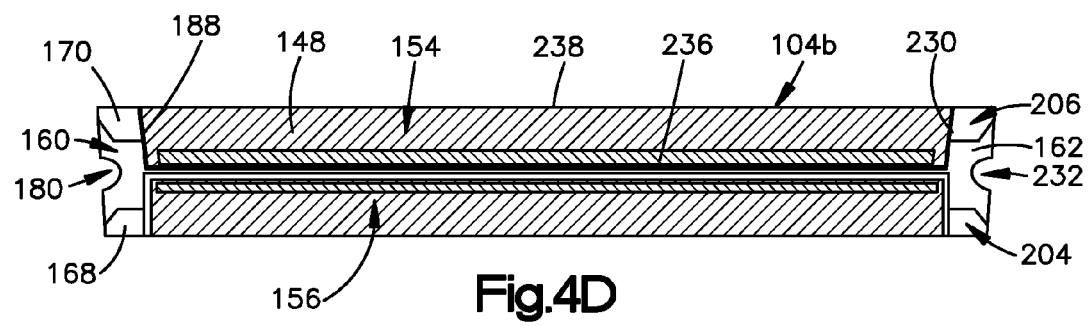
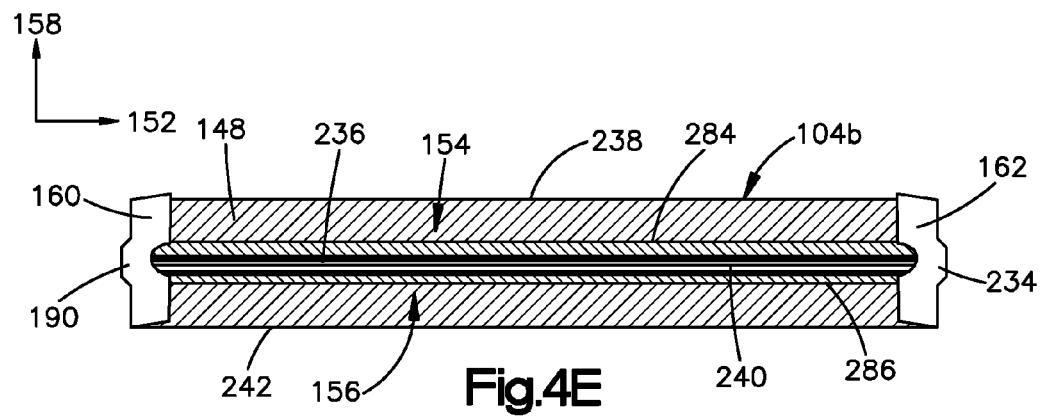
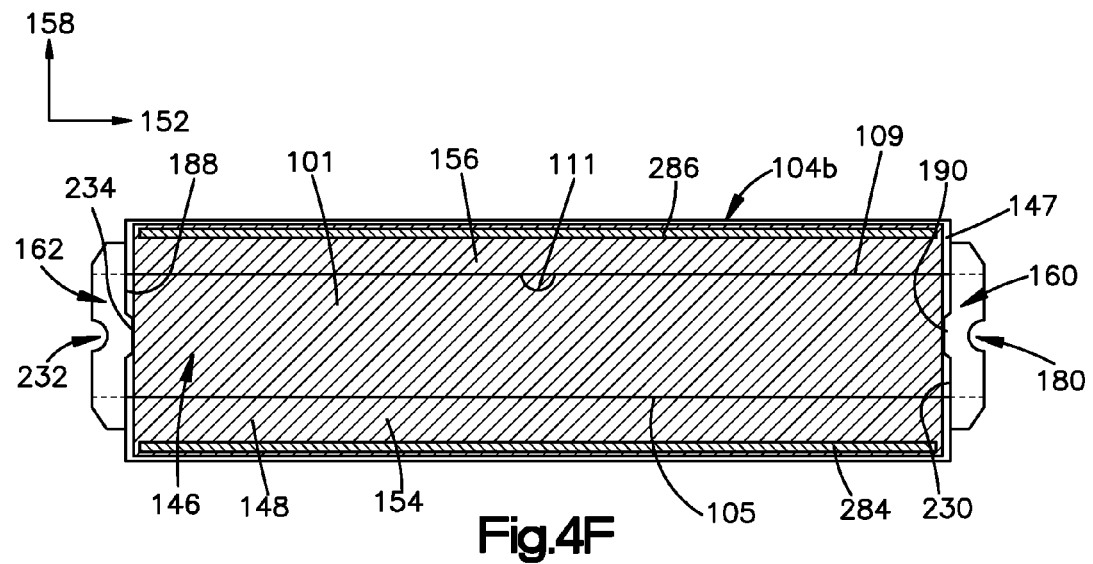

PACKAGE ASSEMBLY

CROSS-REFERENCE TO RELATED APPLICATIONS

This application claims the benefit of U.S. Provisional Patent Application Ser. No. 61/726,132 filed Nov. 14, 2012. The disclosure is hereby incorporated by reference as if set forth in its entirety herein.

TECHNICAL FIELD

The present disclosure relates to assemblies and methods for packaging an object, such as a medical device. More specifically, the present disclosure relates to packaging assemblies for holding an object, methods for making such package assemblies, and methods for packaging an object in such packaging assemblies.

BACKGROUND

Medical devices, such as medical implants, are typically used in a sterile surgical environment. It is thus desirable to deliver medical devices to a surgical site in a sealed package so that sterility is not compromised. To this end, a number of medical device packages and packaging techniques have been developed over the years. Improvements to conventional packages and packaging techniques are still desirable.

A medical device should be packaged so that the integrity of the package is not compromised during delivery to the surgical site. The integrity of the package may be compromised if the medical device punctures the package. Some conventional packages do not fully stabilize the medical device inside the package, thereby increasing the risk of compromising the integrity of the package. It is therefore desirable to develop a package that stabilizes the medical device to prevent, or at least minimize, movement of the medical device inside the package.

It is also desirable to facilitate loading a medical device in a package in order to expedite the packaging process and reduce the risk of compromising the integrity of the package while the medical device is loaded. Some conventional packages require that the medical device be inserted into a relatively small cavity, increasing the risk that the medical device may puncture the package. To avoid puncture the package, the medical device is usually inserted slowly into the small cavity, thereby slowing the packaging process. Hence, it is desirable to develop packages that allow simple insertion of a medical device into the package.

To avoid reselling non-sterile medical devices, many medical device manufacturers do not allow a customer to return a purchased medical device if the packages has been opened. Physicians, however, sometimes need to open a conventional package in order to determine if the medical device is the appropriate size for the patient. These conventional packages do not allow the physician to see the medical device while the package is closed. It is thus desirable to develop a packaging assembly that allows a physician to see the packaged medical device in order to determine whether the packaged medical device is appropriate for the intended medical procedure.

SUMMARY

In an embodiment, the packaging assembly is configured to contain an object. The outer packaging member is configured to have an unassembled configuration and an assembled configuration, the assembled configuration defined as when the object can be contained by the outer packaging member. The outer packing member may include an outer packaging body having a first wall and a second wall spaced from the first wall along a first direction when the outer packaging member is in the unassembled configuration. The outer packaging member defines an outer packaging opening that extends through the outer packaging body along a second direction that is substantially perpendicular to the first direction. Further, the outer packing opening extends from the first wall to the second wall along the first direction when the outer packing body is in the unassembled configuration. The outer packaging member further includes a substantially transparent film that includes 1) attached portions that are attached to the outer packaging body at respective first and second attachment regions of each of the first and second walls, and 2) a cover region that is disposed inboard of the attached portions. The cover region extends across the outer packaging opening, wherein at least a portion of the outer packaging body has a stiffness greater than that of the transparent film. Further, at least one of the first and second walls is pivotable with respect to the cover region about a pivot location that is inboard with respect to at least one of the respective attachment regions. When the at least one of the first and second walls is pivoted about the pivot location, the at least one of the first and second walls extends across at least a portion of the cover region of the transparent film so to place the outer packing body in the assembled configuration.

According to another embodiment, the package assembly includes an outer packaging member configured to have an unassembled configuration and an assembled configuration, the assembled configuration defined as when the object can be contained by the outer packaging member. The outer packing member may include an outer packaging body having a first wall, a second wall spaced from the first wall along a first direction when in the unassembled configuration, and a central wall pivotably coupled to the first wall. Further, the outer packaging member defines an outer packaging opening that extends through the outer packaging body along a second direction that is substantially perpendicular to the first direction. The outer packaging opening extends from the first wall to the second wall along the first direction, wherein the central wall is sized to substantially cover the outer packaging opening. The outer packaging member further includes a substantially transparent film that includes 1) attached portions that is attached to the outer packaging body at respective first and second attachment regions of each of the first and second walls, and 2) a cover region that is disposed inboard of the attached portions, the cover region extending across the outer packaging opening. At least a portion of the outer packaging body has a stiffness greater than that of the transparent film. When the outer packaging member is in the assembled configuration, 1) the central wall substantially covers the outer packaging opening, and 2) at least one of the first and second walls is bent with respect to the outer packing opening about a respective at least one pivot location so as to overly the central wall.

According to another embodiment, the package assembly includes an outer packaging member configured to have an unassembled configuration and an assembled configuration, the assembled configuration defined as when the object can be contained by the outer packaging member. The outer packaging member includes an outer packaging body that includes a first wall and a second wall that each define opposed outer ends that are spaced from each other along a first direction. The first wall is spaced from the second wall along a second direction that is substantially perpendicular to the first direction. At least one of first and second walls being larger than the other of the first and second walls. The outer packaging member defines an outer packaging opening that extends through the outer packaging body along a third direction that is substantially perpendicular to the first and second directions. Further, the opening extends from the first wall to the second wall along the second direction. The outer packaging member further includes a substantially transparent film that includes 1) attached portions that are attached to the outer packaging body at respective first and second attachment regions of each of the first and second walls, and 2) a cover region that extends across the outer packaging opening. The first wall and the second wall are pivotable with respect to the cover region about respective first and second pivot locations that are inboard of the respective first and second attachment regions, such that, the first and second walls extends across at least a portion of the outer packaging opening so as to place the outer packaging member in the assembled configuration.

Another embodiment of the present disclosure is a method of packaging an object with a packaging assembly that includes an inner packaging member, an outer packaging member that includes an outer packaging body, an outer packaging opening that extends through the outer packaging body, and a film that is attached to the outer packaging body and substantially covers the outer packaging opening. The method includes positioning the object inside the inner packaging member. The method further includes placing the inner packaging member on a portion of the film the covers the outer package opening. Portions of the outer packaging can be bent so as to substantially enclose the inner packaging member within the outer packaging member. Bending portions of the outer packaging body causes the film to be pressed against the inner packaging member so as to immobilize the object relative to the outer packaging member.

BRIEF DESCRIPTION OF THE DRAWINGS

The foregoing summary, as well as the following detailed description of a preferred embodiment, are better understood when read in conjunction with the appended diagrammatic drawings. For the purpose of illustrating the invention, the drawings show an embodiment that is presently preferred. The invention is not limited, however, to the specific instrumentalities disclosed in the drawings. In the drawings:

FIG. 1A is a perspective view of a packaging assembly holding an object;

FIG. 1B is a perspective exploded view of the object shown in FIG. 1A and an inner packaging member of the packaging assembly shown in FIG. 1A, wherein the object is being inserted into the inner packaging member;

FIG. 1C is a perspective view of the inner packaging member shown in FIG. 1B with two end portions folded toward a central portion;

FIG. 1D is a top view of an inner surface of an outer packaging member of the packaging assembly shown in FIG. 1A, illustrating the outer packaging member in an unassembled configuration and the inner packaging member shown in FIG. 1B disposed on the outer packing member;

FIG. 1F is a top view of the outer packing member shown in FIG. 1E and the inner packaging member shown in FIG. 1B, wherein the first and second sidewalls of the outer packaging member are bent over the inner packaging member;

FIG. 1G is a top view of the packaging assembly shown in FIG. 1F in an assembled configuration, wherein first and second end walls of the outer packaging member are bent upwardly;

FIG. 1H is a perspective view of the packaging assembly in FIG. 1D, illustrating the assembled packaging assembly being inserted into a container;

FIG. 1I is a perspective end view of the packaging assembly disposed inside the container shown in FIG. 1H;

FIG. 1J is a perspective view of a container without windows;

FIG. 2A is a top view of the inner surface of the outer packaging member shown in FIG. 1C, illustrating an opening;

FIG. 2B is a top view of the outer packing member shown in FIG. 2A that includes a film covering the opening;

FIG. 2C is cross-sectional view of the outer packaging member taken along line 2C-2C in FIG. 2A;

FIG. 3A is a perspective view of a packaging assembly according to another embodiment, the packaging assembly including an inner packaging member and an outer packaging member that includes a first enlarged sidewall, a second sidewall, first and second end walls, an opening, and a film that covers the opening;

FIG. 3B is a perspective view of the outer packaging member shown in FIG. 3A, illustrating the first enlarged sidewall bent over the opening;

FIG. 3C is a top view of the outer packaging member shown in FIG. 3B, depicting the second sidewall of the outer packaging member bent over the first enlarged sidewall;

FIG. 3D is a perspective view of the outer packaging member shown in FIG. 3C, depicting the first and second end walls of the outer packaging member bent upwardly;

FIG. 3E is a bottom view of an outer surface of the outer packing member of the packaging assembly shown in FIG. 3A, illustrating the outer packaging member in an unassembled configuration;

FIG. 4D is a top view of the packaging assembly shown in FIG. 4C, depicting the second sidewall bent over another portion of the central wall;

FIG. 4E is a top view of the packaging assembly shown in FIG. 4D, in an assembled configuration, depicting the first and second end walls bent upwardly;

FIG. 4F is a bottom view of the outer surface of the outer packaging member of the packaging assembly shown in FIG. 4A, illustrating the outer packaging member in an unassembled configuration.

DETAILED DESCRIPTION OF THE DRAWINGS

Figure 1E:
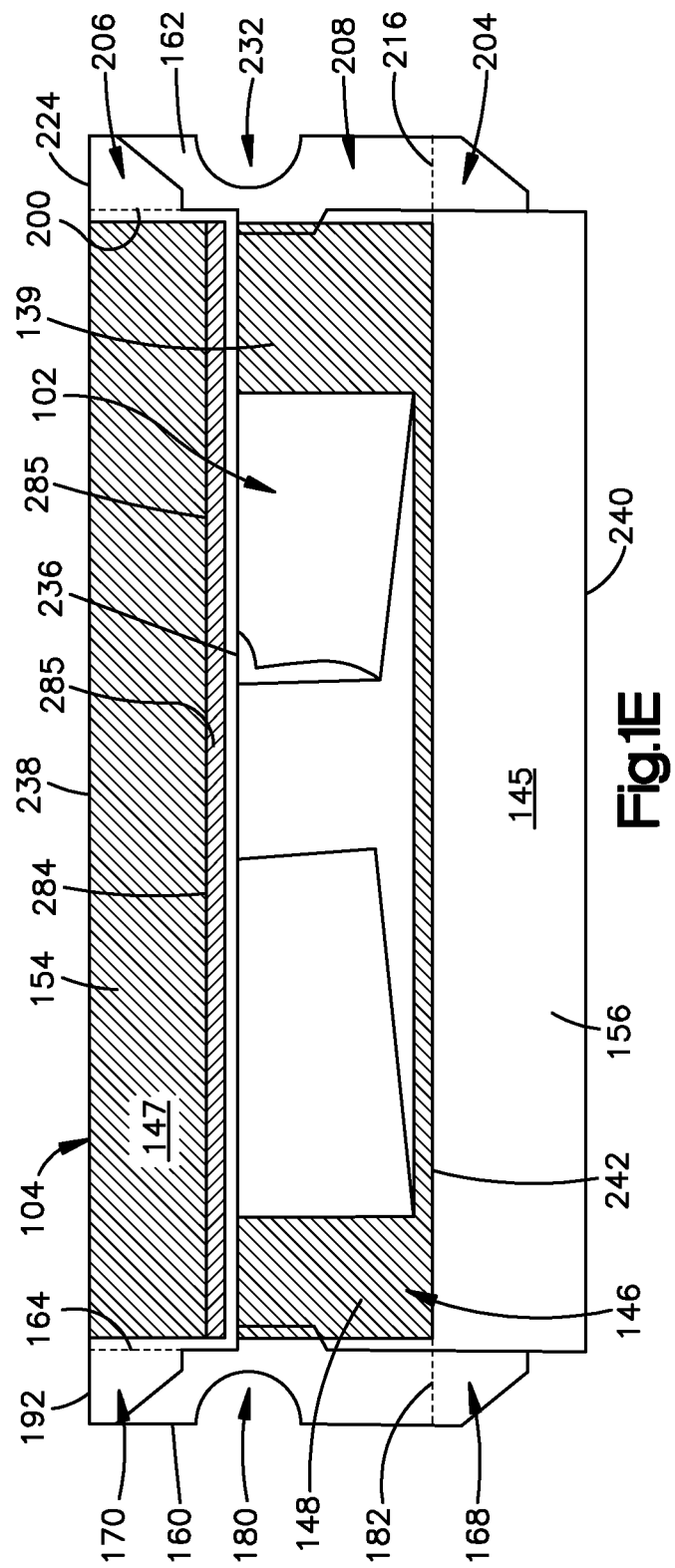
FIG. 1E is a top view of the outer packaging member shown in FIG. 1D and the inner packaging assembly shown in FIG. 1B, wherein the first sidewall of the outer packaging member is bent over the inner packaging member.

Certain terminology is used in the following description for convenience only and is not limiting. The words "right", "left", "lower" and "upper" designate directions in the drawings to which reference is made. The words "longitudinal," "lateral," and "transverse" refer to directional components of the packaging assembly that extend along a length, width, and thickness, of the packaging assembly or components thereof, respectively.

With reference to FIGS. 1A-K, and 2A-B, the present disclosure relates to a packaging assembly 100 that is configured to hold and maintain the position of the object 10 in the packaging assembly 100. While the packaging assembly 100 can be configured to maintain the object 10 in a sterile condition, object 10 sterility is not required. The object 10 may be a medical device 12 such as an intramedullary nail 14 (as illustrated), a bone plate, bone anchor or bone screw, suture, vertebral implant, pedicle screw, spinal fixation rod, or any other suitable device or implant. The object 10 may define a first end 16 and a second end 18. The packaging assembly 100 includes an inner packaging member 102, an outer packaging member 104, and a container 106. The inner packaging member 102 and the outer packaging member 104 cooperate to define a packaging subassembly 115. The inner packaging member 102 is configured to hold object 10. The outer packaging member 104 is configured to hold inner packaging member 102 and the object 10. The container 106 is configured hold the object 10, the inner packaging member 102, and the outer packaging member 104 in an assembled configuration (as discussed in detail below) such that the object 10 is immobilized inside the packaging assembly 100. Immobilizing the object 10 inside the container 106 minimizes the risk of compromising the integrity of the packaging assembly 100. For example, it is less likely that the immobilized object 10 inside the container 106 would puncture a portion of the packaging assembly 100. The packaging assembly 100 can also be configured to allow a user, such as a physician, to view to the packaged object 10 inside the container 106, so that the user can assess the object's characteristics. For example, the user may wish to observe the size of the object 10 before opening the packaging assembly 100. The configuration of the packaging assembly 100 further allows a user to easily load the object 10 inside the packaging assembly 100, thereby expediting the packaging process.

As discussed above, the packaging assembly 100 includes an inner packaging member 102 that is configured to hold the object 10. The inner packaging member 102 includes an inner packaging body 116 and can be configured as a sleeve 118 or a pouch. Further, the inner packaging member 102 defines an inner cavity 120 that is configured and sized to receive the object 10. The inner cavity 120 extends into the inner packaging body 116 and can be elongate along the longitudinal direction 114. The inner packaging body 116 may also be elongate along the longitudinal direction 114 and defines a first closed end 122 and a second open end 124 opposite the first closed end 122. The first closed end 122 is spaced from the second open end 124 along the longitudinal direction 114. The second open end 124 defines an aperture 126 that is in communication with the inner cavity 120. That is, the aperture 126 leads to the inner cavity 120. Accordingly, the object 10 can be inserted into the inner cavity 120 through the aperture 126. The inner packaging member 102 may further define a notch 125 that extends into the inner packaging body 116 at the second open end 124. The notch 125 may have a substantially concave shape and is configured to allow a user to enlarged the aperture 126 in order to facilitate insertion of the object 10 inside the inner packaging member 102. The inner packaging member 102 includes a first inner end portion 138 and a second inner end portion 140 that is spaced from the first inner end portion 138 along the longitudinal direction 114. The first inner end portion 138 is closer to the first closed end 122 than the second open end 124. The second inner end portion 140 is closer to the second open end 124 than to the first closed end 122. The inner packaging member 102 further includes a central inner portion 142 disposed between the first inner end portion 138 and the second inner end portion 140.

The inner packaging body 116 can be wholly or partly made from a substantially flexible material and includes an inner rear portion 108 and an inner front portion 110 opposite the inner rear portion 108. The inner rear portion 108 may be spaced from the inner front portion 110 along a transverse direction 112. The transverse direction 112 may be substantially perpendicular to the longitudinal direction 114. The inner rear portion 108 and the inner front portion 110 can both be elongate along the longitudinal direction 114. The inner rear portion 108 can be connected to the inner front portion 110 along a first inner edge 128 and a second inner edge 130 that is opposite the first inner edge 128. The second inner edge 130 may be spaced from the first inner edge 128 along a lateral direction 132. The lateral direction 132 may be substantially perpendicular to the longitudinal direction 114 and the transverse direction 112. Further, the inner rear portion 108 can be connected to the inner front portion 110 along a third inner edge 134 located at the first closed end 122.

The inner rear portion 108 may be configured as a backing or a substrate 135. The substrate 135 is a substantially flexible material. For instance, the substrate 135 can be medical-grade paper, one or more sheets of nonwoven material, or a laminate of any combination of paper, nonwoven and a film. Further, the substrate 135 can be configured as a barrier material, such as a microbial barrier. The inner rear portion 108 can be wholly or partly made from the barrier material. An exemplary substrate may be a flashspun and bonded high-density polyethylene material (HDPE), sold by Dupont under the trademark Tyvek®. For example, the inner rear portion 108 can be made from any of the HDPE sold by Dupont under the trademarks Tyvek® 1073B, Tyvek® Asuron™, Tyvek® 1059B, or Tyvek® 2FS™. The inner rear portion 108 can be made from a substrate 135 that is a breathable and allows air to travel between the inner cavity 120 and the environment outside the inner packaging member 102. Consequently, the inner packaging member 102 can be compressed during packing process. Hence, the pressure difference between inside and outside the inner packaging member 102 does not need to be considered when packaging the object 10 in the packaging assembly 100. Further, the substrate 135 can be substantially opaque.

The inner front portion 110 can be made of a substantially transparent or translucent material. For example, the inner front portion 110 can be wholly or partly formed from one or more a substantially transparent or translucent stretch film 136, which is also known as stretch wrap. In turn, the stretch film 136 can be wholly or partly made of a linear low-density material is linear low-density polyethylene (LLDPE) or any other suitable polymer. The stretch film 136 may also be wholly or partly made of polyester film sold under the trademark MYLAR® by Dupont. The transparency of the inner front portion 110 allows a user to observe the object 10 even when the object 10 is disposed inside the inner packaging member 102. The inner front portion 110 can be coated with an antimicrobial coating. Any other suitable coating can be applied to the inner front portion 110.

Initially, the object 10 can be inserted in the inner cavity 120 through the aperture 126 as shown in FIG. 1A Specifically, the object 10 can be moved in a direction 15 toward the aperture 126 until the entire object 10 is disposed in the inner cavity 120. Once the object 10 is disposed in the inner cavity 120, the first inner end portion 138 is folded so that the first inner end portion 138 is disposed over the central inner portion 142. Similarly, the second inner end portion 140 is folded so that the second inner end portion 140 is disposed over the central inner portion 142 as shown in FIG. 1B. The first inner end portion 138 and the second inner end portion 140 can be folded as described above in order to secure the object 10 within the inner packaging member 102.

After placing the object 10 in the inner cavity 120 and folding the first inner end portion 138 and the second inner end portion 140, the inner packaging member 102 can be placed on the outer packaging member 104 in an unassembled configuration. The outer packaging member 104 includes an outer packaging body 144 and an outer packaging opening 146 that extends through the outer packaging body 144. The outer packaging opening 146 allows quick positioning and loading of the object 10 during packaging the object 10. The outer packaging body 144 may include an inner surface 145 and an opposed outer surface 147. The outer surface 147 is spaced from the inner surface 145 along a transverse direction 153 when the outer packaging member 104 is in an unassembled configuration (FIG. 2C). The transverse direction 153 may be referred to as the third direction herein. The unassembled configuration is illustrated in FIGS. 1D, 2B, 2C, 3E, 4F and 5. When the outer packing member 104 is an assembled configuration, the outer surface 147 is exposed while the inner surface 145 at least partially defines an inner cavity that holds the inner packaging member 102. It should be appreciated, that outer packaging body 144 may be initially configured as a blank 150 that has a substantially planar configuration in the unassembled configuration For instance, in the unassembled configuration, the outer packaging body 144 or blank 150 may have a substantially flat configuration. The outer packaging body 144 is wholly or partly made of a substantially rigid material. The rigid material may be paperboard, corrugated cardboard, or plastic. Further, the rigid material may be a laminate of two or more layers of paperboard, cardboard, or plastic. Alternatively, the rigid material may be a laminate of any combination of paperboard, cardboard, or plastic.

In the embodiment depicted in FIGS. 1A-K, 2A-2C, the outer packaging body 144 can be elongate along a longitudinal direction 152 and includes a first outer sidewall 154 and a second outer sidewall 156 opposite the first outer sidewall 154. The first outer sidewall 154 and the second outer sidewall 156 can also be referred as first and second walls, respectively. The second outer sidewall 156 may be spaced from the first outer sidewall 154 along a lateral direction 158 that is substantially perpendicular to the longitudinal direction 152. The longitudinal direction 152 may be referred as a first direction when the lateral direction is referred to as a second direction. Further, the lateral direction 158 may be referred to as a first direction when the longitudinal direction 152 is referred to the second direction. Thus, it can be said that the second outer sidewall 156 is spaced from the first outer sidewall 154 along the second direction. The first outer sidewall 154 and the second outer sidewall 156 may both be elongate along the longitudinal direction 152. In the depicted embodiment, the first and second outer sidewalls 154, 156 can have a substantially rectangular shape. However, it is envisioned that the first and second outer sidewalls 154, 156 may have other shapes.

The outer packaging body 144 further includes a first outer end wall 160 and a second outer end wall 162 opposite the first outer end wall 160. The first outer end wall 160 can also be referred to as a first tab, and the second outer end wall 162 can also be referred to as the second tab. The second outer end wall 162 can be spaced from the first outer end wall 160 along the longitudinal direction 152. The first outer end wall 160 and the second outer end wall 162 are both elongate along the lateral direction 158. The first outer end wall 160 can be pivotally coupled to the first outer sidewall 154 through a first bending line 164. The first bending line 164 can be configured as a living hinge, one or more scores, a combination thereof, or any structure that allows the first outer end wall 160 to pivot relative to the first outer sidewall 154. Regardless of its configuration, the first bending line 164 allows the first outer end wall 160 to be pivoted relative to the first outer sidewall 154. The first outer end wall 160 can be pivotally connected to the second outer sidewall 156 through a second bending line 166. The second bending line 166 can be configured as a living hinge, a score, a combination thereof, or any structure that allows the first outer end wall 160 to pivot relative to the second outer sidewall 156.

The first outer end wall 160 further includes a first end portion 168, a second end portion 170, and a first central portion 172 that is disposed between the first end portion 168 and the second end portion 170. The first end portion 168 may define a first edge 174 that is elongate along the longitudinal direction 152. The first edge 174 can be directly connected to the second outer sidewall 156. The first end portion 168 may further define a second edge 176 that is connected to the first edge 174. The second edge 174 can be elongate along a direction that is oblique relative to the longitudinal direction 152 and the lateral direction 158. The first end portion 168 further defines a third edge 178 that is connected to the second edge 176. The third edge 178 can be elongate along the lateral direction 158 and can be directly connected to the second edge 176 and the first central portion 172. The first end portion 168 can be pivotally coupled to the first central portion 172 through a third bending line 182. The third bending line 182 can be configured as a living hinge, one or more scores, a combination thereof, or any structure that allows the first end portion 168 to pivot relative to the first central portion 172.

The first central portion 172 can be disposed between the first end portion 168 and the second end portion 170 and includes a first central body 184. The first central body 184 defines a first central outer edge 186 and a first central inner edge 188 that is opposite the first central outer edge 186. The first central inner edge 188 can be spaced from the first central outer edge 186 along the longitudinal direction 152. The first central portion 172 further defines a first notch 180 that extends into the first central body 184 and may have a substantially concave shape. In the depicted embodiment, the first notch 180 extends into the first central outer edge 186 of the first central body 184. The first notch 180 can be configured and sized to receive a finger. In operation, a user can insert a finger in the notch 180 to grab and pivot the first outer end wall 160 relative to the first outer sidewall 154 and the second outer sidewall 156. The first central portion 172 further includes a first protrusion 190 that protrudes from the first central body 184. In the depicted embodiment, the first protrusion 190 can protrude from the first central inner edge 188 in the longitudinal direction 152. In operation, the first protrusion 190 can contact an inner surface of the container 106 to fix the position of the outer packaging member 104 with respect to the container 106 when the outer packaging member 104 is disposed inside the container 106 and the object 10 is inside the outer packaging member 104, thereby immobilizing the object 10 inside the container 106. The first central outer edge 186 can be referred to as a first tab end, and the first protrusion 190 can also be referred to as a second tab end.

The second end portion 170 can be pivotally coupled to the first central portion 172 through a fourth bending line 192. The fourth bending line 192 can be configured as a living hinge, one or more scores, a combination thereof, or any structure that allows the second end portion 170 to pivot relative to the first central portion 172. The second end portion 170 may further define a first edge 194 that is elongate along the longitudinal direction 152. The first edge 194 can be directly connected to the first outer sidewall 154. The second end portion 170 may further define a second edge 196 that is connected to the first edge 194. The second edge 196 can be elongate along a direction that is oblique relative to the longitudinal direction 152 and the lateral direction 158. The second end portion 170 may further include a third edge 198 that is connected to the second edge 196. The third edge 198 can be elongate along the lateral direction 158 and can be directly connected to the first central portion 172.

The second outer end wall 162 can be pivotally coupled to the first outer sidewall 154 through a fifth bending line 200. The fifth bending line 200 can be configured as a living hinge, one or more scores, a combination thereof, or any structure that allows the second outer end wall 162 to pivot with respect to the first outer side wall 154. The second outer end wall 162 can also be pivotally coupled to the second outer sidewall 156 through a sixth bending line 202. The sixth bending line 202 can be configured as a living hinge, one or more scores, a combination thereof, or any structure that allows the second outer end wall 162 to pivot relative to the second outer sidewall 156.

The second outer end wall 162 includes a first end portion 204, a second end portion 206, and a second central portion 208 that is disposed between the first end portion 204 and the second end portion 206. The first end portion 204 may define a first edge 210 that is elongate along the longitudinal direction 152. The first edge 210 can be directly connected to the second outer sidewall 156. The first end portion 204 may further define a second edge 212 that is connected to the first edge 210. The second edge 212 can be elongate along a direction that is oblique relative to the longitudinal direction 152 and the lateral direction 158. The first end portion 204 may further define a third edge 214 that is connected to the second edge 212. The third edge 212 can be elongate along the lateral direction 158 and can be directly connected to the second central portion 208. The first end portion 204 can be pivotally coupled to the second central portion 208 through a seventh bending line 216. The seventh bending line 216 can be configured as a living hinge, one or more scores, a combination thereof, or any structure that allows the first end portion 204 to pivot relative to the second central portion 208.

The second end portion 206 of the second outer end wall 162 may define a first edge 218 that is elongate along the longitudinal direction 152. The first edge 218 can be directly connected to the first outer sidewall 154. The second end portion 206 may further define a second edge 220 that is connected to the first edge 218. The second edge 220 can be elongate along a direction that is oblique relative to the longitudinal direction 152 and the lateral direction 158. The second end portion 206 may further define a third edge 222 that is connected to the second edge 220. The third edge 212 can be elongate along the lateral direction 158 and can be directly connected to the second central portion 208. The second end portion 206 can be pivotally coupled to the second central portion 208 through an eight bending line 224. The eight bending line 224 can be configured as a living hinge, one or more scores, a combination thereof, or any structure that allows the second end portion 206 to pivot relative to the second central portion 208.

The second central portion 208 can be disposed between the first end portion 204 and the second end portion 206 and includes a second central body 226. The second central body 226 defines a second central outer edge 228 and a second central inner edge 230 that is opposite the second central outer edge 228. The second central inner edge 230 can be spaced from the second central outer edge 228 along the transverse direction 152. The second central portion 208 further defines a second notch 232 that extends into the second central body 226. In the depicted embodiment, the second notch 232 extends into the second central outer edge 228 and may have a substantially concave shape. The second notch 232 can be configured and sized to receive a finger. In operation, a user can insert a finger in the second notch 232 to grab and pivot the second outer end wall 162 relative to the first outer sidewall 154 and the second outer sidewall 156. The second central portion 208 may further include a second protrusion 234 that protrudes from second central body 226. In the depicted embodiment, the second protrusion 234 protrudes from the second central inner edge 230 in the longitudinal direction 152. In operation, the second protrusion 234 can contact an inner surface of the container 106 to secure the position of the outer packaging member 204 relative to the container 106 when the outer packaging member 104 is disposed inside the container 106, thereby immobilizing the object 10 that is inside the container 106. The second central outer edge 228 can be referred to as a first tab end, while the second protrusion 234 can also be referred to as a second tab end.

The first outer sidewall 154 is connected between the first outer end wall 160 and the second outer end wall 162 and defines a first sidewall outer edge 236 and an opposed first sidewall inner edge 238. The first sidewall inner edge 238 can be substantially aligned with the fourth bending line 192 and the eight bending line 224 so that the first outer sidewall 154 can be pivoted relative to the first outer end wall 160 and the second outer end wall 162 about the first sidewall inner edge 238. Pivoting the first outer sidewall 154 about the first sidewall inner edge 238 causes the second end portion 170 of the first outer end wall 160 to pivot about the fourth bending line 192 and the second end portion 206 of the second outer end wall 162 to pivot about the eight bending line 224. The first sidewall outer edge 236 may be spaced from the first edge 218 of the second end portion 206 along the lateral direction 158. In the depicted embodiment, the first outer sidewall 154 can be sized and configured to cover at least a portion of the outer packaging opening 146 when the first outer sidewall is pivoted about the first sidewall inner edge 238.

The second outer sidewall 156 is connected between the first outer end wall 160 and the second outer end wall 162 and defines a second sidewall outer edge 240 and an opposed second sidewall inner edge 242. The second sidewall inner edge 242 can be substantially aligned with the third bending line 182 and seventh bending line 216 so that the second outer sidewall 156 can be pivoted relative to the first outer end wall 160 and the second outer end wall 162 about the second sidewall inner edge 242. Pivoting the second outer sidewall 156 about the second sidewall inner edge 242 causes the first end portion 168 of the first outer end wall 160 to pivot about the third bending line 182 and the first end portion 204 of the first outer end wall 162 to pivot about the seventh bending line 216. The second sidewall outer edge 240 may be spaced from the first edge 210 of the second outer end wall 162 and the first edge 174 of the first outer end wall 160. In the depicted embodiment, the second outer sidewall 156 can be sized and configured to cover at least a portion of the outer packaging opening 146 when the second outer sidewall 156 is pivoted about the second sidewall inner edge 242.

As discussed above, the outer packaging member 104 defines at least one outer packaging opening 146 that extends through the outer packaging body 144. The outer packing opening 146 can be created by cutting a blank using any suitable technology. For instance, the blank can be die cut to create the outer packaging opening 146. The outer packaging opening 146 is completely surrounded by the outer packaging body 144. Specifically, the first outer sidewall 154, the second outer sidewall 156, the first outer end wall 160, and a second outer end wall 162 cooperate to surround the outer packaging opening 146. The outer packaging opening 146 defines a first end 131 and an opposed second end 132 (FIG. 2C) that is spaced from the first end 131 along the transverse direction 153. The transverse direction 153 may be substantially perpendicular to the lateral direction 158 and the longitudinal direction 153. The transverse direction 153 also defines a placement trajectory.

The outer packaging opening 146 extends through the outer packaging body 144 along a transverse direction 153 that is substantially perpendicular to the lateral direction 158 and the longitudinal direction 152. The transverse direction 153 may be referred to as the second direction. Moreover, the outer packaging opening 146 may extend from the first outer sidewall 154 to the second outer sidewall 156 along the lateral or second direction 158. Further still, the outer packaging opening 146 may extend from the first outer end wall 160 to the second outer end wall 162 along the longitudinal direction 152. The longitudinal direction 152 may be referred to as the third direction.

The outer packaging member 104 includes a substantially transparent or translucent film 148 that substantially covers the entire outer packaging opening 146. In the depicted embodiment, the film 148 may be configured as a stretch film and may be attached to the outer surface 147 of the outer packaging body 144 using any suitable techniques such as an adhesive. For instance, the film 148 may be attached to portions of the first outer sidewall 154, the second outer sidewall 156, the first outer end wall 160, the second outer end wall 160, or any combination thereof. In the depicted embodiment, the film 148 can be attached to the first outer sidewall 154 along a first attachment region 284 and to the second outer sidewall 154 along a second attachment region 286. The film 148 includes a first attached portion 285 that is attached to the first attachment region 284 and a second attached portion 287 that is attached to the second attachment region 286. Thus, the film 148 can be attached to the outer packaging body 144 at respective first and second attachment regions 284, 286 of each of the first outer sidewall 154 and the second outer sidewall 156. The film 148 further includes a cover region 139 that is disposed inboard of the attached portions 284, 286. The cover region 139 extends across the first end 131 of the outer packaging opening.

The film 148 can be wholly or partly made of a linear low-density material is linear low-density polyethylene (LL-DPE), a polyester film, such as the polyester film sold under the trademark MYLAR® by Dupont polymer, a combination thereof, or any other suitable polymer. The film 148 can be coated with an antimicrobial coating or any other suitable coating. As noted above, the film 148 can be attached to the first outer sidewall 154 and the second outer sidewall 156. Additionally or alternatively, the film 148 can be attached to the first end portion 168 and the second end portion 170 of the first outer end wall 160 and to the first end portion 204 and the second end portion 206 of the second outer end wall 162. It is envisioned that the film 148 can also be attached to other portions of the first outer end wall 160 and the second outer end wall 162. At least a portion of the film 148 can be disposed over the first protrusion 190 and the second protrusion 234 when the outer packaging member 104 is in the unassembled configuration. The film 148 is configured to stretch over the inner packaging member 102 when the inner packaging member 102 is disposed on the film 148 and the first outer sidewall 154 and the second outer sidewall 156 are pivoted toward the outer packaging opening 146. At least a portion of the outer packaging body 144 may have a stiffness that is greater than the stiffness of the film 148. Further, it should be appreciated that when the outer packing body 106 is formed two or more layers of the rigid material (not shown), the film 148 can attached between two layers of the rigid material at attachment regions defined by adjacent surfaces of the respective two layers rigid material.

As discussed above, the object 10 can be first inserted into the inner cavity 120 of the inner packaging member 102 through the aperture 126. The object 10 should be placed inside the inner packaging member 102 such that the first end 16 of the object is spaced from the inner rear portion 108 and the second end 18 of the object 10 is spaced from the second open end 124. Once the object 10 is entirely disposed inside the inner packaging member 102, the first inner end portion 138 is bent over the central inner portion 142 of the inner packaging member 102, and the second end portion 140 is bent over the inner central portion 142 to secure the object 10 inside the inner packaging member 102 as shown in FIG. 1C. Next, the inner packaging member 102 is placed on the outer packaging member 104. Specifically, the inner packaging member 102 can be disposed on the film 148 such that no portion of the inner packaging member 102 extends beyond the boundaries of the outer packaging opening 146 as shown in FIG. 1D.

Then, the first outer sidewall 154 is pivoted along the first sidewall inner edge 238 such that at least a portion of the first outer sidewall 154 is disposed over at least a portion of the outer packing opening 146 and thus the cover region 139. When the inner packaging member 102 as shown in FIG. 1E is placed on the film 148 aligned with the opening 146, the first outer sidewall 154 is disposed over the at least a portion of the inner packaging member 102. Pivoting the first outer sidewall 154 about the first sidewall inner edge 238 causes the second end portion 170 of the first outer end wall 160 to pivot about the fourth bending line 192 such that the second end portion 170 is disposed over the first central portion 172. In addition, pivoting the first outer sidewall 154 about the first sidewall inner edge 238 causes the second end portion 206 of the second outer end wall 162 to pivot about the eight bending line 224 such that the second end portion 206 is disposed over the second central portion 208. Moreover, pivoting the first outer sidewall 154 causes the film 148 to stretch, causing the film 148 to press against the inner packaging member 102 to immobilize the inner packaging member 102 relative to the outer packaging member 104. In brief, the first outer side wall 154 is pivotable with respect to the cover region 139 about a first pivot location 239, which is defined by the second sidewall inner edge 238. The first pivot location 239 is inboard with respect to the first attachment region 284 along the lateral direction 158. Such that the first outer sidewall 154 can pivot about the first pivot location 239 so as to at least partially cover the outer packaging opening 146. In the depicted embodiment, where the film 148 is attached to the outer surface 147, when the first outer side wall 154 has been pivoted or bent along the first pivot location 239, the first outer sidewall 154 at least partially extends across the second end of the outer packing opening 146.

Next, the second outer sidewall 156 is pivoted along the second sidewall inner edge 242 such that at least a portion of the second outer sidewall 156 is disposed over the inner packaging member 102 as shown in FIG. 1F. Pivoting the second outer sidewall 156 about the second sidewall inner edge 242 causes the first end portion 168 of the first outer end wall 160 to pivot about the third bending line 182 such that the first end portion 168 is disposed over the first central portion 172. Moreover, pivoting the second outer sidewall 156 about the second sidewall inner edge 242 causes the first end portion 204 of the second outer end wall 162 to pivot about the seventh bending line 216 such that the first end portion 204 of the second outer end wall is at least partially disposed over the second central portion 208. Further, pivoting the first outer sidewall 154 and the second outer sidewall 156, such that they cover the inner packing member 102, causes the film 148 to stretch over the inner packaging member 102, thereby immobilizing the inner packaging member 102 inside the outer packaging member 104. That is, the inner packaging member 102 and the object 10 are substantially enclosed between the film 148 and the first outer sidewall 154 and the second outer sidewall 156. In other words, pivoting the first outer sidewall 154 and the second outer sidewall 156, such that they cover the inner packing member 102, causes the film 148 to press against the inner packaging member 102 such that the inner packaging member 102 is immobilize relative to the outer packaging member 104. In brief, the second outer side wall 156 is pivotable with respect to the cover region 139 about a second pivot location 243, which is defined by the second sidewall inner edge 242. The second pivot location 243 is inboard with respect to the second attachment region 286 along the lateral direction 158 when the outer packing member is in the unassembled configuration. When the second sidewall 156 is pivoted or bent about the second pivot location 243, the second outer sidewall 156 at least partially covers outer packaging opening 146. For instance, in the depicted embodiment when the film 148 is attached to the outer surface 147 and the second outer sidewall 156 is pivoted about the second pivot location 243, the second outer sidewall 156 extends across at least a portion of the second end 132 of the outer packaging opening 146. When the first outer side wall 154 and the second outer sidewall 156 are both pivoted as shown in FIG. 1G, the first outer sidewall 154 or the second outer sidewall 156 extends across at least a portion of the outer packaging opening 146 along the lateral direction 158. Further, it should be appreciated also that when the first outer side wall 154 and the second outer sidewall 156 are both pivoted as shown in FIG. 1G, at least a portion of the outer packaging opening 146 extends along the transverse direction 153 between the film 148 and at least one of the first outer sidewall 154 or the second outer sidewall 156.

Then, the first outer end wall 160 can be pivoted about the first central inner edge 188 as shown in FIG. 1G. Pivoting the first outer end wall 160 about the first central inner edge 188 causes the first end portion 168 to pivot about the second bending line 166. Furthermore, pivoting the first outer end wall 160 causes the second end portion 170 to pivot about the first bending line 164. Next, the second outer end wall 162 can be pivoted about the second central inner edge 230 as shown in FIG. 1G. Pivoting the second outer end wall 162 about the second central inner edge 230 causes the first end portion 204 to pivot about the sixth bending line 202. Further, pivoting the second outer end wall 162 about the second central inner edge 230 causes the second end portion 206 to pivot about the fifth bending line 200. At this point, the outer packaging member 104 is in the assembled configuration.

Subsequently, the outer packaging member 104 is inserted in the container 106. The container 106 may be configured as a box 107. In the depicted embodiment, the container 106 may have a substantially cuboid shape and include a container body 248 and an inner cavity 256 that extends into the container body 248. The container body 248 may be elongate along a longitudinal direction 266 and includes a first container sidewall 250 and an opposed second container sidewall 252. The first container sidewall 250 may be spaced from the second container sidewall 252 along a lateral direction 258. The container body 248 may further include a front container wall 260 and an opposed rear container wall 262. The rear container wall 262 may be spaced from the front container wall 260 along a transverse direction 264 that is substantially perpendicular to the lateral direction 258. The container 106 may include one or more container holes 268 that extend into the container body 248. In the depicted embodiment, the container holes 268 extend through the front container wall 260. One or more transparent or translucent films 270 are attached to the container body 248 and cover the container holes 268. The translucent or transparent film 270 allows a user to visualize the object 10 even when it is packed inside the packaging assembly 100. Visualization of the object 10 inside the packaging assembly 100 allows the user to determine if the object 10 has the appropriate size for the intended medical procedure. Alternatively, the packaging assembly 100 may include a container 106A that does not include container holes 268 as shown in FIG. 1J. The container 106 also includes a first end cap 272 and a second end cap that is spaced from the first end cap 272 along the longitudinal direction 266. The container body 248 defines an outer container surface 276 and an opposed inner container surface 280. The inner container surface 280 defines an inner container cavity 282 that is sized and configured to receive the object 10, the inner packaging member 102, and the outer packaging member 104 in the assembled configuration. As discussed above, after the outer packaging member 104 has been placed in the assembled configuration, it is inserted in the inner container cavity 282 of the container 106. The container 106 may be closed by, for example, closing the container end cap 274.

Referring to FIGS. 3A-E, a packaging assembly 100A is substantially similar to the packaging assembly 100. However, the packaging assembly 100A includes an outer packaging member 104A, wherein one of the first outer sidewall 154 or the second outer sidewall 156 is larger than the other so that the larger sidewall is sized to cover the entire inner packaging member 102 when the inner packaging member 102 is placed on the film 148 as discussed above. In the depicted embodiment, the first outer sidewall 154A may be larger than the second outer side wall 156. The first outer sidewall 154A defines a first transverse dimension L1 that extends from first sidewall outer edge 236 to opposed first sidewall inner edge 238 along the lateral direction 158. The second outer sidewall 156 defines a second transverse dimension L2 that extends from the second sidewall outer edge 240 to the second sidewall inner edge 242 along the lateral direction 158. The first transverse dimension L1 is larger than the second transverse direction L2. Thus, the first outer sidewall 154A can be configured and sized to be pivoted along the first sidewall inner edge 238 so as to cover the entire inner packaging member 102 that is disposed on the film 148. The first outer sidewall 154A may also include a ninth bending line 155 that is elongate along the longitudinal direction 152. The ninth bending line 155 may be disposed between the first sidewall outer edge 236 and the first sidewall inner edge 238 and allows the first outer sidewall 154A to bending so as to at least partly conform to the shape of the object 10 and the inner packaging member 102. The ninth bending line 155 divides the first outer sidewall 154A into a first sidewall portion and a second sidewall portion. The first sidewall portion 159 is spaced from the second sidewall portion 161 along the lateral direction 158 when the outer packaging member 104A is in the unassembled configuration. The ninth bending line 155 can be configured as a living hinge, one or more scores, a combination thereof, or any structure that allows the second sidewall portion 161 to pivot relative to the first sidewall portion 159.

With continued reference to FIGS. 3A-E, the film 148 can be attached to the first outer sidewall 154A along the first attachment region 284. The first attachment region 284 may include an adhesive that attaches a portion of the film 148 to the first outer sidewall 154A. In the depicted embodiment, the first attachment region 284 is elongate along the longitudinal direction 152 and may be disposed between the first sidewall outer edge 236 and the first sidewall inner edge 238. The film 148 can be attached to the second outer sidewall 156 along the second attachment region 286. The second attachment region 286 may include an adhesive that attaches a portion of the film 148 to the second outer sidewall 156. In the depicted embodiment, the second attachment region 286 can be elongate along the longitudinal direction 152 and may be disposed closer to the second sidewall outer edge 240 than to the second sidewall inner edge 242. The film 148 defines a first film end 149 and an opposed second film end 151 that is spaced from the first film end 149 along the longitudinal direction 152. Moreover, the film 148 does not overlap the first protrusion 190 and the second protrusion 234 so the first outer end wall 160 and the second outer end wall 162 can be pivoted toward the outer surface 147. Specifically, the first film end 149 is spaced from the first protrusion 190 along the longitudinal direction 152, and the second film end 151 is spaced from the second protrusion 234 along the longitudinal direction 152.

The method of assembling the packaging assembly 100A is similar to the packaging method described above with respect to the packaging assembly 100. The object 10 is first inserted into the inner packaging member 102 as described above. Then, the inner packaging member 102 that contains the object 10 is disposed over the film 148 as shown in FIG. 3A. Then, the first outer sidewall 154A is pivoted about the first sidewall inner edge 238 so that it entirely covers the inner packaging member 102 as shown in FIG. 3B. Subsequently, the second outer sidewall 156 is pivoted about the second sidewall inner edge 242 so as to cover a portion of the first outer sidewall 154A. Pivoting the first outer sidewall 154A and the second outer sidewall 156 toward the inner packaging member 102 causes the stretch film 102 to stretch around the inner packaging member 102. Next, the first outer end wall 160 can be pivoted about the first central inner edge 188 as shown in FIG. 3D so that the first outer end wall 160 is oriented at a non-zero angle relative to the first outer sidewall 154A and the second outer sidewall 156. Similarly, the second outer end wall 162 can be pivoted about the second central inner edge 230 as shown in FIG. 3D so that the second outer end wall 162 is oriented at a non-zero angle relative to the first outer sidewall 154A and the second outer sidewall 156. At this point, the outer packaging member 100A is in an assembled configuration. The assembled outer packaging member 100A can then be inserted into the container 106 or the container 106A.

With reference to FIGS. 4A-F, a packaging assembly 100B is substantially similar to the packaging assembly 100. However, the packaging assembly 100B includes an outer packaging member 104B that includes a central wall 101 that is pivotally coupled to first outer sidewall 154 or the second outer sidewall 156. In the depicted embodiment, the central wall 101 may be pivotally coupled to the first outer sidewall 154 along the first sidewall inner edge 238. Thus, the central wall 101 can be pivoted relative to the first outer sidewall 154 about the first sidewall inner side edge 238. The central wall 101 is configured and sized to cover substantially the entire outer packaging opening 146. In the depicted embodiment, the central wall 101 includes a central wall body 103 that defines a first central wall end 105 and a second central wall end 109 that is spaced from the first central wall end 109 along the lateral direction 158. The first central wall end 105 can be pivotally couple to the first outer sidewall 154. The central wall 101 may further define a notch 111 that extends into the central wall body 103. Specifically, the notch 111 may extent into the second central wall end 109 and may have a substantially concave shape. In use, the notch 111 helps a user hold the central wall 101 in order to pivot the central wall 101 relative to the first outer sidewall 154. The film 148 can be connected to the inner surface 147 of the outer packaging body 144 to allow the central wall 101 to freely pivot relative to the first outer sidewall 154.

Figure 4A:
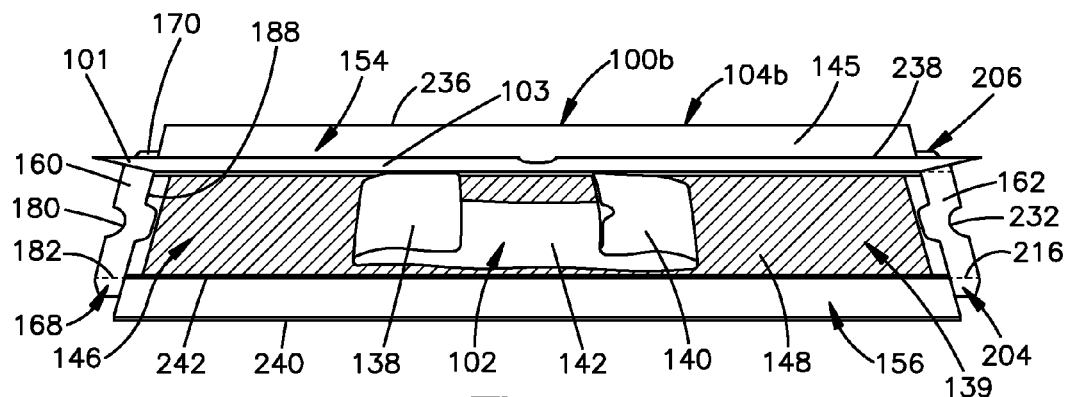
FIG. 4A is a perspective view of a packaging assembly according to another embodiment of the present disclosure, the packaging assembly including an inner packaging member and an outer packing member that includes first and second sidewalls, first and second end walls, an opening, a film that covers the opening, and a central wall that is movably coupled to the first sidewall.
Figure 4B:
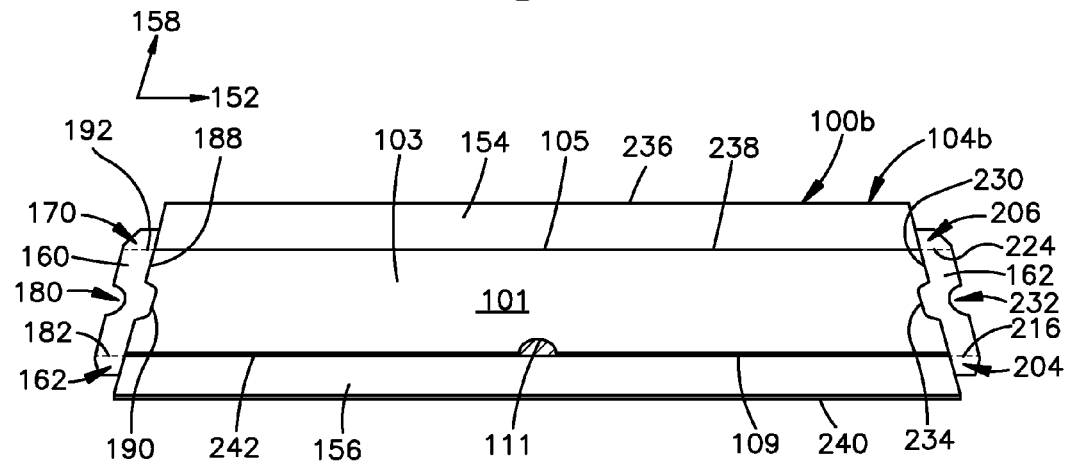
FIG. 4B is a perspective view of the packaging assembly shown in FIG. 4A, depicting the central wall of the outer packing member bent over the inner packaging member.
Figure 4C:
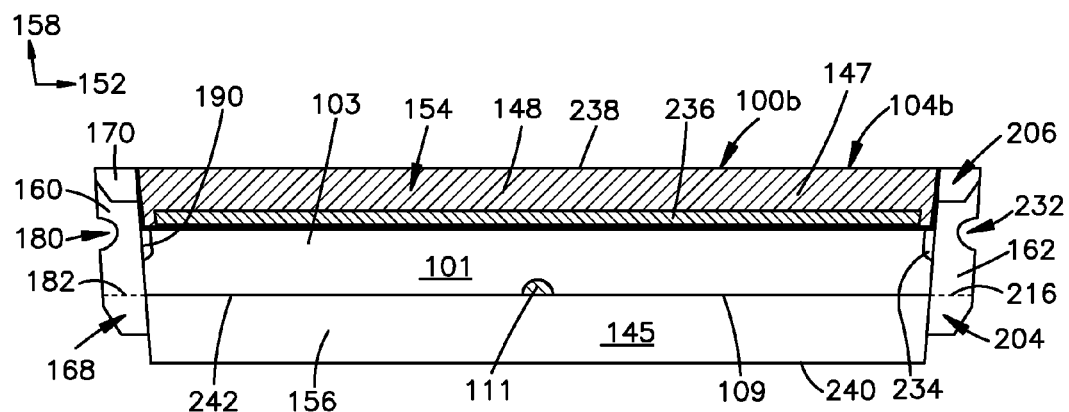
FIG. 4C is a top view of the packaging assembly shown in FIG. 4B, depicting the first sidewall of the outer packaging member bent over a portion of the central wall.

The method of assembling the packaging assembly 100B is similar to the method of assembling the packaging assembly 100. The object 10 is inserted in the inner packaging member 102 as described above. Then, the inner packaging member 102 is placed on the film 148 as shown in FIG. 4A. The central wall 101 is subsequently pivoted about the first sidewall inner side edge 238 to cover the inner packaging member 102 with the central wall 101 as shown in FIG. 4B. Next, the first outer sidewall 154 can be pivoted about the first sidewall inner side edge 238 such that the first outer sidewall 154 overlaps a portion of the central wall 101. Then, the second outer sidewall 156 can be pivoted about the second sidewall inner edge 242 so that the second outer sidewall 156 overlaps another portion of the central wall 101 as shown in FIG. 4D. Then, the first outer end wall 160 can be pivoted about the first central inner edge 188 as shown in FIG. 4E. Further, the second outer end wall 162 can be pivoted about the second central inner edge 230 as shown in FIG. 4E. The outer packaging assembly 104B can then be inserted into a container 106 or 106a as discussed above.

Figure 5:
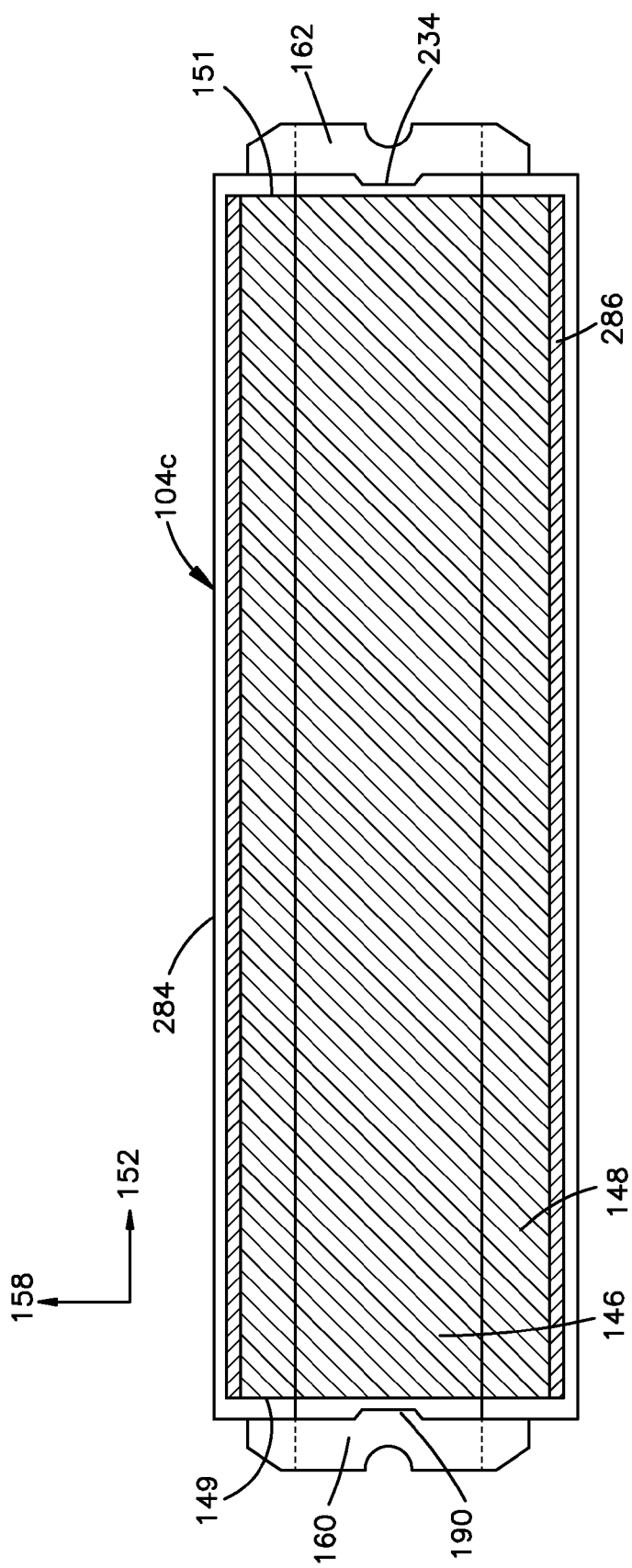
FIG. 5 is a top view of an outer packaging member of a packaging assembly in accordance with another embodiment of the present disclosure.

With reference to FIG. 5, an outer packaging member 104C is substantially similar to the outer packaging member 104. However, in this embodiment, the film 148 does not overlap the first protrusion 190 and the second protrusion 234 so the first outer end wall 160 and the second outer end wall 162 can be pivoted toward the outer surface 147 to facilitate pivoting of the first outer end wall 160 and the second outer end wall 162 relative to the first outer sidewall 154 and the second outer sidewall 156. Specifically, the first film end 149 is spaced from the first protrusion 190 along the longitudinal direction 152, and the second film end 151 is spaced from the second protrusion 234 along the longitudinal direction 152.

In accordance with another embodiment of the present disclosure, the outer packaging member 104, 104B and 104C can be manufactured from planar sheet of the rigid material. The planar sheet can be shaped into the blank 150 defining the outer packing body 104 having the first and second sidewalls, the first and second opposed end walls, and the outer packaging opening as described above. For instance, shaping the planar sheet into the blank 150 can include cutting the planar sheet to have the configuration of the outer packing member body described above. Cutting can include blades, rotary blades, lasers or any other cutting technique. For instance, the method can including cutting the planar sheet to define the opening 146. In an embodiment, the cutting can include cutting the planar sheet, or the blank 150, to define the central wall. The transparent film can be attached to blank 150 such that the film cross the opening. In alternate embodiments, the transparent film is disposed between adjacent layers of the rigid material that have the opening 146 precut therein. The blank 150 can then be used for packaging the object as described herein.

It should be noted that the illustrations and discussions of the embodiments shown in the figures are for exemplary purposes only, and should not be construed limiting the disclosure. One skilled in the art will appreciate that the present disclosure contemplates various embodiments. For instance, one or more of the walls described in the present disclosure can be configured as panels. Moreover, the protrusions described herein can be configured as locking tabs. It should be further appreciated that the features and structures described and illustrated in accordance one embodiment can apply to all embodiments as described herein, unless otherwise indicated. Additionally, it should be understood that the concepts described above with the above-described embodiments may be employed alone or in combination with any of the other embodiments described above.

What is claimed:

1. A package assembly configured to contain an object, the package assembly comprising:
    an outer packaging member configured to have an unassembled configuration and an assembled configuration, the assembled configuration defined as when the outer packaging member contains the object, the outer packaging member including an outer packaging body having a first wall, a second wall spaced from the first wall along a first direction when in the unassembled configuration, a first outer end wall, and a second outer end wall opposed to the first outer end wall, wherein the first outer end wall is configured to pivot relative to the first and second walls and the second outer end wall is configured to pivot relative to the first and second walls, the outer packaging member defining an outer packaging opening that extends through the outer packaging body along a second direction that is substantially perpendicular to the first direction, the outer packaging opening extending from the first wall to the second wall along the first direction when the outer packaging body is in the unassembled configuration, the outer packaging member further including a substantially transparent film that includes 1) attached portions that are attached to the outer packaging body at respective first and second attachment regions of each of the first and second walls, and 2) a cover region that is disposed inboard of the attached portions, the cover region extending across the outer packaging opening, wherein at least a portion of the outer packaging body has a stiffness greater than that of the transparent film, wherein at least one of the first and second walls is pivotable with respect to the first and second outer end walls about a respective pivot location that is inboard with respect to at least one of the respective attachment regions, and when the at least one of the first and second walls is pivoted about the respective pivot location, the at least one of the first and second walls at least partially covers at least a portion of the outer packaging opening and extends across at least a portion of the cover region of the transparent film so as to place the outer packaging member in the assembled configuration; and
    a container that includes a container outer surface, an opposed container inner surface, and a container cavity substantially defined by the container inner surface, the container cavity configured to receive the outer packaging member,
    wherein at least one of the first outer end wall and the second outer end wall is configured to pivot so as to contact the container inner surface to immobilize the outer packaging member relative to the container when the outer packaging member is disposed in the container cavity.

2. The package assembly of claim 1, wherein pivoting the at least one of the first and second walls with respect to the cover region increases a level of tension of the cover region of the transparent film.

3. The packaging assembly of claim 1, further comprising an inner packaging member that defines a cavity, the cavity configured to receive the object.

4. The packaging assembly of claim 3, wherein the outer packaging member is configured to substantially enclose the inner packaging member such that the transparent film is pressed against the inner packaging member so as to immobilize the object relative to the inner packaging member and the outer packaging member when 1) the object is disposed in the inner cavity, and 2) the outer packaging member in the assembled configuration and substantially encloses the inner packaging member.

5. The packaging assembly of claim 3, wherein the outer packaging member defines a placement trajectory of the inner packaging member along a direction that extends through the opening and against the cover region, the direction of the placement trajectory being angularly offset with respect to the first direction.

6. The packaging assembly of claim 1, wherein the first wall, the second wall, the first outer end wall, and the second outer end wall cooperate to define the outer packaging opening when the outer packing member is in the unassembled configuration.

7. The packaging assembly of claim 1, wherein the first outer end wall includes a central body and a protrusion that protrudes from the central body, the protrusion configured to contact the container inner surface to immobilize the outer packaging member relative to the container.

8. The packaging assembly of claim 1, wherein a portion of the container is made from a substantially transparent material to allow visualization of the object when the object, the inner packaging member, and the outer packaging member are disposed in the container cavity.

9. The packaging assembly of claim 1, wherein the first wall is larger than the second wall such that the first wall substantially covers the outer packaging opening.

10. The packaging assembly of claim 1, wherein the outer packaging body further comprises a central wall that is pivotally coupled to the first wall, and the central wall is configured to substantially cover the outer packaging opening.

11. The package assembly of claim 1, wherein the outer packaging opening extends from the first outer end wall to the second outer end wall along a third direction that is substantially perpendicular to the first direction.

12. A package assembly configured to contain an object, the package assembly comprising:
an outer packaging member configured to have an unassembled configuration and an assembled configuration, the assembled configuration defined as when the outer packaging member contains the object, the outer packaging member including an outer packaging body having a first wall, a second wall spaced from the first wall along a first direction when in the unassembled configuration, a first outer end wall, and a second outer end wall opposed to the first outer end wall, wherein the first outer end wall is configured to pivot relative to the first and second walls and the second outer end wall is configured to pivot relative to the first and second walls, the outer packaging member defining an outer packaging opening that extends through the outer packaging body along a second direction that is substantially perpendicular to the first direction, the outer packaging opening extending from the first wall to the second wall along the first direction when the outer packaging body is in the unassembled configuration, the outer packaging member further including a substantially transparent film that includes 1) attached portions that are attached to the outer packaging body at respective first and second attachment regions of each of the first and second walls, and 2) a cover region that is disposed inboard of the attached portions, the cover region extending across the outer packaging opening, wherein at least a portion of the outer packaging body has a stiffness greater than that of the transparent film, wherein at least one of the first and second walls is pivotable with respect to the first and second outer end walls about a respective pivot location that is inboard with respect to at least one of the respective attachment regions, and when the at least one of the first and second walls is pivoted about the respective pivot location and at least one of the first and second outer end walls is pivoted with respect to the first and second walls, the at least one of the first and second walls extends across at least a portion of the cover region of the transparent film so as to place the outer packaging member in the assembled configuration, such that at least a portion of the outer packaging opening extends between at least one of the first and second walls and at least a portion of the cover region along the second direction, and the at least a portion of the outer packaging opening extends between at least one of the first and second outer end walls and the portion of the cover region along the second direction; and
a container that includes a container outer surface, an opposed container inner surface, and a container cavity substantially defined by the container inner surface, the container cavity configured to receive the outer packaging member,
wherein when the at least one of the first and second outer end walls pivots with respect to the first and second walls, the at least one of the first and second outer end walls is configured to contact the container inner surface to immobilize the outer packaging member relative to the container when the outer packaging member is disposed in the container cavity.

13. The package assembly of claim 12, wherein pivoting the at least one of the first and second walls with respect to the cover region increases a level of tension of the cover region of the transparent film.

14. The package assembly of claim 13, wherein the at least one of the first and second walls is the second wall, and the second wall is pivotable with respect to the cover region about the pivot location that is inboard with respect to the second attachment region such that the second wall at least partially extends across the outer packaging opening.

15. The packaging assembly of claim 12, further comprising an inner packaging member that defines a cavity, the cavity configured to receive the object.

16. The packaging assembly of claim 15, wherein the outer packaging member is configured to substantially enclose the inner packaging member such that the transparent film is pressed against the inner packaging member so as to immobilize the object relative to the inner packaging member and the outer packaging member when 1) the object is disposed in the inner cavity, and 2) the outer packaging member in the assembled configuration and substantially encloses the inner packaging member.

17. The packaging assembly of claim 15, wherein the outer packaging member defines a placement trajectory of the inner packaging member along a direction that extends through the opening and against the cover region, the direction of the placement trajectory being angularly offset with respect to the first direction.

18. The packaging assembly of claim 12, wherein the first wall, the second wall, the first outer end wall, and the second outer end wall cooperate to define the outer packaging opening when the outer packing member is in the unassembled configuration.

19. The packaging assembly of claim 12, wherein the first outer end wall includes a central body and a protrusion that protrudes from the central body, the protrusion configured to contact the container inner surface to immobilize the outer packaging member relative to the container.

20. The packaging assembly of claim 12, wherein a portion of the container is made from a substantially transparent material to allow visualization of the object when the object, the inner packaging member, and the outer packaging member are disposed in the container cavity.

21. The packaging assembly of claim 12, wherein the first wall is larger than the second wall such that the first wall substantially covers the outer packaging opening.

22. The packaging assembly of claim 12, wherein the outer packaging body further comprises a central wall that is pivotally coupled to the first wall, and the central wall is configured to substantially cover the outer packaging opening.

23. A package assembly configured to contain an object, the package assembly comprising:
an outer packaging member configured to have an unassembled configuration and an assembled configuration, the assembled configuration defined as when the outer packaging member contains the object, the outer packaging member including an outer packaging body having a first wall, a second wall spaced from the first wall along a first direction when in the unassembled configuration, a first outer end wall, and a second outer end wall opposed to the first outer end wall, wherein the first outer end wall is configured to pivot relative to the first and second walls and the second outer end wall is configured to pivot relative to the first and second walls, the outer packaging member defining an outer packaging opening that extends through the outer packaging body along a second direction that is substantially perpendicular to the first direction, the outer packaging opening extending from the first wall to the second wall along the first direction when the outer packaging body is in the unassembled configuration, the outer packaging member further including a substantially transparent film that includes 1) attached portions that are attached to the outer packaging body at respective first and second attachment regions of each of the first and second walls, and 2) a cover region that is disposed inboard of the attached portions, the cover region extending across the outer packaging opening, wherein at least a portion of the outer packaging body has a stiffness greater than that of the transparent film, wherein at least one of the first and second walls is pivotable with respect to the first and second outer end walls about a respective pivot location that is inboard with respect to at least one of the respective attachment regions, and when the at least one of the first and second walls is pivoted about the respective pivot location and at least one of the first and second outer end walls is pivoted with respect to the first and second walls, the at least one of the first and second walls extends across at least a portion of the cover region of the transparent film so as to place the outer packaging member in the assembled configuration, and the at least one of the first and second outer end walls extends across at least a portion of the outer packaging opening; and a container that includes a container outer surface, an opposed container inner surface, and a container cavity substantially defined by the container inner surface, the container cavity configured to receive the outer packaging member, wherein when the at least one of the first and second outer end walls pivots with respect to the first and second walls, the at least one of the first and second outer end walls is configured to contact the container inner surface to immobilize the outer packaging member relative to the container when the outer packaging member is disposed in the container cavity.

* * * * *